United States Patent [19]

Aoki et al.

[11] Patent Number: 5,962,493
[45] Date of Patent: Oct. 5, 1999

[54] 2-MERCAPTOBENZIMIDAZOLE DERIVATIVES AND ANTIHYPERLIPEMIC AGENT OR ANTIARTERIOSCLEROTIC AGENT CONTAINING THE SAME

[75] Inventors: Kozo Aoki; Kazuhiro Aikawa, both of Minami-Ashigara, Japan

[73] Assignee: Fuji Photo Film Co., Ltd., Kanagawa-ken, Japan

[21] Appl. No.: 08/975,638

[22] Filed: Nov. 21, 1997

Related U.S. Application Data

[62] Division of application No. 08/669,516, filed as application No. PCT/JP95/00116, Jan. 30, 1995, abandoned.

[51] Int. Cl.$^6$ .................................................. A61K 31/415
[52] U.S. Cl. ......................... 514/394; 514/395; 514/824
[58] Field of Search ................................. 514/394, 395, 514/824

[56] References Cited

U.S. PATENT DOCUMENTS 3,704,130  11/1972  Pollet et al. ........................ 96/114.7

FOREIGN PATENT DOCUMENTS

0520552 A1  12/1992  European Pat. Off. ...... C07H 19/167
0583665 A2  2/1994  European Pat. Off. ....... A61K 31/05

OTHER PUBLICATIONS

O.P. Suri et al., "Synthesis and Spectral Studies of 2–Mercaptobenzimidazole Derivatives II" *J. Heterocyclic Chem.* 20:813 (1983).

C.A. Johnson et al., "Synthesis of Some New Lead Trypanocidal Compounds Belonging to the Mercaptobenzazole Series" *Med. Chem. Res.* 2:247–255 (1992).

PCT International Search Report dated Mar. 28, 1995 corresponding to USSN 08/669,516.

T. Xin et al., "Synthesis and Antiparasitic Activity of 2–Alkyl=Thiobenzimidazoles", *Chemical Abstracts* 114:766, No. 114:143240m (1991).

S. Kumar et al., "Heterocyclic Systems Containing Bridgehead Nitrogen Atom" *Chemical Abstracts* 114:723, No. 114:81703d (1991).

H.K. Pujari et al., "Heterocyclic Systems Containing Bridgehead Nitrogen Atoms" *Chemical Abstracts* 113:770, No. 113:78240z (1990).

T.R. Lee et al., "Synthesis and Reactions of Benzimidazoline–2–Thione Derivatives" *Chemical Abstracts* 111:750, No. 111:57628a (1989).

R. Dahiya et al., "Heterocyclic Systems Containing A Bridgehead Nitrogen Atom" *Chemical Abstracts* 111:749, No. 111:57623v (1989).

A.K. Bagrii et al., "Synthesis of [1,3]Thiazino[3,2–a]Imidazole and Its Condensed Analogs" *Chemical Abstracts* 84:485, No. 84:43959w (1976).

A.N. Krasovskii et al., "Imidazoles. XLII. Synthesis of Thiazolino[3,2–a]–Benzimidazole and Some of Its Derivatives" *Chemical Abstracts* 70:324, No. 47349f (1969).

W. Wroblewski et al., "Ag+–Selective Electrodes Based of Lipophilic Thioethers" *Chemical Abstracts* 123:1503, No. 123:305287x (1995).

*Primary Examiner*—Kevin E. Weddington
*Attorney, Agent, or Firm*—Testa, Hurwitz & Thibeault LLP

[57] ABSTRACT

2-Mercaptobenzimidazole derivatives represented by the following formulae, analogs and salts thereof are disclosed:

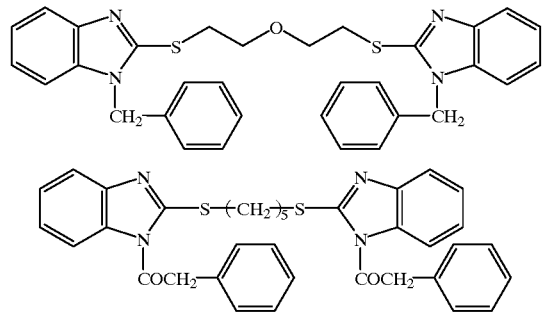

These 2-mercaptobenzimidazole derivatives are useful as a medicine such as an antihyperlipemic agent or antiarteriosclerotic agent and also useful as an additive for silver halide photosensitive materials, liquid crystals and the like.

10 Claims, No Drawings

2-MERCAPTOBENZIMIDAZOLE DERIVATIVES AND ANTIHYPERLIPEMIC AGENT OR ANTIARTERIOSCLEROTIC AGENT CONTAINING THE SAME

This is a divisional application of U.S. Ser. No. 08/669,516, filed on Jul. 12, 1996, now abandoned which was a 35 U.S.C. §371 filing of PCT/JP95/00116, filed on Jan. 30, 1995 which claims priority under 35 U.S.C. §119 to JP 12876/1994, filed on Feb. 4, 1994, JP 12877/1994, filed on Feb. 4, 1994, JP 77519/1994, filed on Apr. 15, 1994, and JP 176805/1994, filed on Jul. 28, 1994.

TECHNICAL FIELD

The present invention relates to 2-mercaptobenzimidazoles, in particular, bis-type 2-mercaptobenzimidazole compounds. The 2-mercaptobenzimidazole compounds are usable as medicines such as antihyperlipemic and antiarteriosclerotic agents and additives for silver halide photosensitive materials, for liquid crystals and the like.

In particular, the 2-mercaptobenzimidazole derivatives of the present invention are capable of preventing macrophages from foaming which causes arteriosclerosis.

BACKGROUND OF THE INVENTION

As the standard of living is being raised, foods having a high colory and high cholesterol content are increasing in our eating habits. Furthermore, aging society is now being advanced to accelerate the increase in the number of patients suffering from hyperlipemia and arteriosclerosis caused by hyperlipemia. This is a serious social problem.

In the pharmacotherapy for hyperlipemia and arteriosclerosis, the reduction in the lipid concentration in the blood is mainly conducted, but no medicine capable of reducing the arteriosclerotic nidi per se has been developed yet.

Since patients suffering from arteriosclerosis have characerisic lesions, i. e. thickening of intima and cumulation of lipids, medicines effective in reducing the lipid concentration in the blood are used in the pharmacotherapy as described above. However, on the basis of the recent biochemical knowledge, it has been found that foaming of macrophages is a main cause for the formation of the arteriosclerotic lesions. It is, therefore, expected that the arteriosclerotic lesions per se can be reduced by inhibiting the foaming of macrophages.

DISCLOSURE OF THE INVENTION

The object of the present invention is to provide new compounds effective for the treatment of patients suffering from hyperlipemia and arteriosclerosis.

Another object of the present invention is to provide an antihyperlipemic agent or an antiarteriosclerotic agent.

The above-described objects and other objects of the present invention will be apparent from the following description and Examples.

After investigations made for the purpose of attaining the above-described objects, the inventors have found that a specified benzimidazole compound has an ACAT inhibition effect, effect of inhibiting tire transportation of cholesterol in the cells, excellent effect of decreasing the blood cholesterol and effect of inhibiting the foaming of macrophages. The present invention has been completed on the basis of this finding.

In the first embodiment of the present invention, there are provided 2-mercaptobenzimidazole derivatives represented by the following formulae I to III or salts thereof:

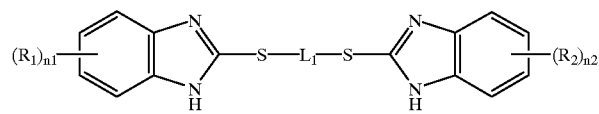

I

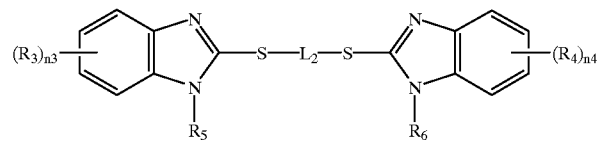

II

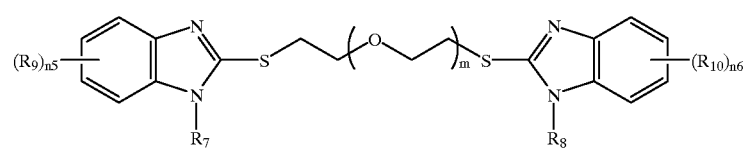

III wherein $R_1$ and $R_2$ each represent an alkyl group or halogen atom;

$R_3$ and $R_4$ each represent a hydrogen atom, halogen atom, or alkyl, alkoxy, alkoxycarbonyl, carbamoyl, sulfamoyl, acylamino, sulfonylamino, cyano or nitro group;

$R_5$ and $R_6$ each represent an alkyl group or acyl group;

$R_7$ and $R_8$ each represent a hydrogen atom, alkyl group or alkylcarbonyl group, $R_9$ and $R_{10}$ each represent a hydrogen atom, halogen atom, nitro group or alkyl group;

$n_1$, $n_2$, $n_3$, $n_4$, $n_5$ and $n_6$ each represent 1 or 2, m represents 1, 2 or 3; and $L_1$ and $L_2$ each represent a connecting group which is an alkylene group or phenylene group-containing alkylene group, and when $L_1$ is a pentamethylene group, both $R_1$ and $R_2$ may be hydrogen atoms.

In the second embodiment of the present invention, there is provided an antihyperlipemic agent or an antiarteriosclerotic agent containing a 2-mercaptobenzimidazole derivative represented by the above formula III or the following formula IV or a salt thereof and a diluent and/or excipient:

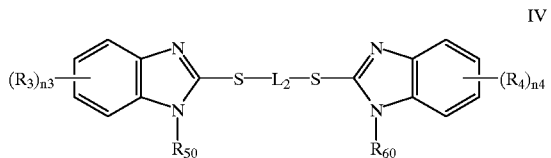

wherein $R_3$, $R_4$, $n_3$, $n_4$ and $L_2$ are as defined in the above formula II, and $R_{50}$ and $R_{60}$ each represent a hydrogen atom, alkyl group or acyl group.

THE BEST MODE FOR CARRYING OUT THE INVENTION

The detailed description will be made on the compounds of the present invention.

In the formula I, the alkyl groups represented by $R_1$ and $R_2$ include those having 1 to 18 carbon atoms (such as methyl, ethyl, butyl, octyl, dodecyl and octadecyl groups), preferably those having 1 to 8 carbon atoms (such as methyl, ethyl, butyl and octyl groups). Particularly preferred alkyl groups are those having 1 to 3 carbon atoms (such as methyl, ethyl, propyl and trifluoro groups). The alkyl-groups may be linear, branched or cyclic alkyl groups which may have a substituent. The halogen atoms include fluorine, chlorine, bromine and iodine atoms. Among them, fluorine, chlorine and bromine atoms are preferred. Chlorine atom is particularly preferred. When $L_1$ is a pentamethylene group, both $R_1$ and $R_2$ may be hydrogen atoms.

In the formula II, the halogen atoms represented by $R_3$ and $R_4$ include fluorine, chlorine, bromine and iodine atoms. Among them, fluorine, chlorine and bromine atoms are preferred. Chlorine atom is particularly preferred. The alkyl groups include those having 1 to 18 carbon atoms (such as methyl, butyl, octyl, dodecyl and octadecyl groups), preferably those having 1 to 8 carbon atoms (such as methyl, ethyl, butyl and octyl groups). Particularly preferred alkyl groups are those having 1 to 3 carbon atoms (such as methyl, ethyl, propyl and trifluoro groups). The alkoxy groups include those having 1 to 18 carbon atoms (such as methoxy, butoxy, octyloxy, dodecyloxy and octadecyloxy groups), preferably those having 1 to 8 carbon atoms (such as methoxy, ethoxy, butoxy and octyloxy groups). Particularly preferred alkoxy groups are those having 1 to 3 carbon atoms. The alkoxy-carbonyl groups include those having 1 to 18 carbon atoms (such as methoxycarbonyl, butoxycarbonyl, octyloxycarbonyl, d odecyloxycarbonyl and octadecyloxy-carbonyl groups), preferably those having 1 to 8 carbon atoms (such as methoxycarbonyl, ethoxycarbonyl, butoxy-carbonyl and octyloxycarbonyl groups). Particularly preferred alkoxycarbonyl groups are those having 1 to 3 carbon atoms. The carbamoyl groups include those having 0 to 18 carbon atoms (such as carbamoyl, methylcarbamoyl, diethylcarbamoyl, octylcarbamoyl, hexadecylcarbamoyl and phenylcarbamoyl groups), preferably those having 0 to 8 carbon atoms (such as methylcarbamoyl, diethylcarbamoyl and octylcarbamoyl groups).

The sulfamoyl groups include those having 0 to 18 carbon atoms (such as sulfamoyl, methylsulfamoyl, diethylsulfamoyl, octylsulfamoyl, hexadecylsulfamoyl and phenylsulfamoyl groups), preferably those having 0 to 8 carbon atoms (such as sulfamoyl, methylsulfamoyl, diethylsulfamoyl and octylsulfamoyl groups). The acylamino groups include those having 1 to 18 carbon atoms (such as acetylamino, butanoylamino, octanoylamino, hexadecanoylamino and benzoylamino groups), preferably those having 1 to 8 carbon atoms (such as acetylamino, butanoylamino and octanoylamino groups). The sulfonylamino groups include those having 1 to 18 carbon atoms (such as methanesulfonylamino, butanesulfonylamino, octanesulfonylamino, hexadecanesulfonylamiono and benzenesulfonylamino groups), preferably those having 1 to 8 carbon atoms (such as methanesulfonylamino, butanesulfonylamino, octanesulfonylamino and benzenesulfonylamino groups). These alkyl groups may be linear, branched or cyclic and the alkyl and aryl groups may further have a substituent.

Among them, the halogen atoms, alkyl groups, alkoxy groups, alkoxycarbonyl groups, sulfamoyl groups and nitro group are preferred.

In the formula II, the alkyl groups represented by $R_5$ and $R_6$ include those having 1 to 18 carbon atoms (such as methyl, ethyl, butyl, octyl, dodecyl and octadecyl groups), preferably those having 1 to 8 carbon atoms (such as methyl, ethyl, butyl and octyl groups), which may be either linear or branched. The acyl groups include alkanoyl, arylcarbonyl, alkylsulfonyl, arylsulfonyl, alkoxycarbonyl, sulfamoyl and carbamoyl groups. The alkanoyl groups include those having 1 to 18 carbon atoms (such as acetyl, butanoyl, octanoyl and octadecanoyl groups), preferably those having 1 to 8 carbon atoms (such as acetyl, butanoyl and octanoyl groups). The alkanoyl groups may be linear, branched or cyclic, and the alkyl or aryl group may further have a substituent. The arylcarbonyl groups include those having 6 to 18 carbon atoms (such as benzoyl and naphthoyl groups) which may further have a substituent. The alkoxycarbonyl groups include those having 1 to 18 carbon atoms (such as methoxycarbonyl, ethoxycarbonyl, octyloxycarbonyl and octadecylcarbonyl groups), preferably those having 1 to 8 carbon atoms (such as methoxycarbonyl, ethoxycarbonyl and octyloxycarbonyl grups). The alkoxycarbonyl groups may be linear, branched or cyclic, and they may further have a substituent.

The alkylsulfonyl groups and arylsulfonyl groups include those having 1 to 18 carbon atoms and those having 6 to 18 carbon atoms, respectively, (such as methanesulfonyl, butanesulfonyl, hexadecanesulfonyl, benzenesulfonyl and naphthalenesulfonyl groups) which may further have a substituent. The alkoxycarbonyl groups include those having 1 to 18 carbon atoms (such as methoxycarbonyl, ethoxycarbonyl, octyloxycarbonyl and tetradecyloxycarbonyl groups), preferably those having 1 to 8 carbon atoms (such as methoxycarbonyl, ethoxycarbonyl and octyloxycarbonyl groups) which may further have a substituent. The sulfamoyl groups include those having 0 to 18 carbon atoms (such as sulfamoyl, methylsulfamoyl, diethylsulfamoyl, octylsulfamoyl, hexadecylsulfamoyl and phenylsulfamoyl groups), preferably those having 0 to 8 carbon atoms (such as sulfamoyl, methylsulfamouyl, diethylsulfamoyl and octylsulfamoyl groups) which may further have a substituent. The carbamoyl groups include those having 0 to 18 carbon atoms (such as carbamoyl, methylcarbamoyl, diethylcarbamoyl, octylcarbamoyl, hexadecylcarbamoyl and phenylcarbamoyl groups), preferably those having 0 to 8 carbon atoms (such as methylcarbamoyl, diethylcarbamoyl and octylcarbamoyl groups) which may further have a substituent.

The acyl groups are preferably alkanoyl, arylcarbonyl, alkylsulfonyl, alkoxycarbonyl and carbamoyl groups.

In the formulae I and II, the alkylene groups represented by $L_1$ and $L_2$ include those having 4 to 10 carbon atoms (such as 1,4-butylene, 1,5-pentylene, 1,6-hexylene and 1,10-dodecylene groups), preferably those having 4 to 8 carbon atoms (such as 1,4-butylene, 1,5-pentylene, 1,6-hexylene and 1,8-octylene groups) which may further have a substituent. The connecting group consisting of an alkylene group including phenylene group is a divalent alkylene-phenylene-alkylene group (such as 1,4-xylylene, 1,3-xylylene, 1,2-xylylene or 2-ethylidene-4-phenylmethyl group).

The compounds represented by the formulae I and III may form a salt. The salts which can be formed by these compounds include, for example, hydrochlorides, bromates, nitrates, sulfates, phosphates and toluenesulfonates.

The particularly preferred compounds of the formula I are those of the following formula I-I:

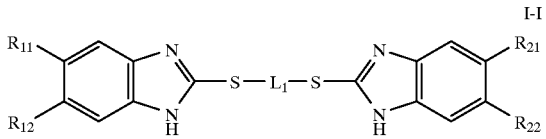

I-I wherein $L_1$ is as defined above, $R_{11}$, $R_{12}$, $R_{21}$ and $R_{22}$ each represent a hydrogen atom, alkyl group or halogen atom, with the proviso that both of $R_{11}$ and $R_{12}$, and $R_{21}$ and $R_{22}$ cannot be hydrogen atoms.

The alkyl groups represented by $R_{11}$, $R_{12}$, $R_{21}$ and $R_{22}$ in the formula I-I are those having 1 to 18 carbon atoms (such as methyl, ethyl, butyl, octyl, dodecyl and octadecyl groups), preferably those having 1 to 8 carbon atoms (such as methyl, ethyl, butyl and octyl groups). The alkyl groups may be linear, branched or cyclic, and they may further have a substituent. The alkyl groups are particularly preferably those having 1 to 3 carbon atoms (such as methyl, ethyl, propyl and trifluoro groups). The halogen atoms include fluorine, chlorine, bromine and iodine atoms. Among them, fluorine, chlorine and bromine atoms are preferred. Chlorine atom is particularly preferred.

In the formula I-I, $R_{11}$ is preferably the same as $R_{12}$, and $R_{21}$ is preferably the same as $R_{22}$.

Other particularly preferred compounds of the formula I are those of the following formula I-a:

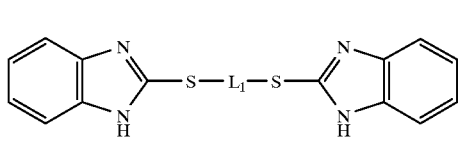

I-a wherein $L_1$ represents a pentamethylene group.

The particularly preferred compounds of the formula II are those of the following formula II-I:

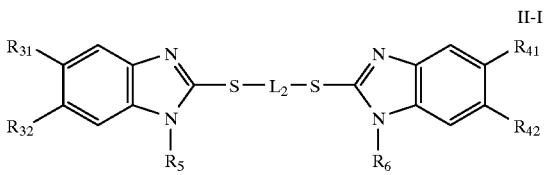

II-I wherein $L_2$, $R_5$ and $R_6$ are as defined above, $R_{31}$, and $R_{32}$ are the same as $R_3$, and $R_{41}$ and $R_{42}$ are the same as $R_4$.

In the formula II-I, $R_5$ and $R_6$ are preferably the same as each other.

In the formula II-I, it is preferred that the combination of $R_{31}$ and $R_{32}$ is the same as the combination of $R_{41}$ and $R_{42}$ (namely, $R_{31}=R_{41}$ and $R_{32}=R_{42}$ or $R_{31}=R_{42}$ and $R_{32}=R_{41}$). Preferred substituents in the formula II are those in the formula II-I.

Among the compounds of the formula II-I, those of the following groups (i) to (iii) are particularly preferred from the viewpoint of the pharmacological effect:

(i) Compounds in which one of $R_{31}$ and $R_{32}$ and one of $R_{41}$ and $R_{42}$ are hydrogen and the other is a lower alkyl, halogen (particularly chlorine), nitro or lower acylamino, and each of $R_5$ and $R_6$ is a lower alkyl or lower alkanoyl.

(ii) Compounds in which all of $R_{31}$, $R_{32}$, $R_{41}$ and $R_{42}$ are hydrogen, and each of $R_5$ and $R_6$ is a lower alkanoyl or lower alkyl. $L_2$ is desirably an alkylene group having 4 to 10 carbon atoms, preferably 4 to 8 carbon atoms. Namely, $L_2$ is preferably an alkylene-phenylene-alkylene group (the alkylene having desirably 1 to 2 carbon atoms).

(iii) Compounds in which each of $R_{31}$, $R_{32}$, $R_{41}$ and $R_{42}$ is a halogen (particularly chlorine) or lower alkyl, and each of $R_5$ and $R_6$ is a lower alkanoyl or lower alkyl group.

$L_2$ in the above-described compounds (i) and (iii) is desirably an alkylene group having 4 to 10 carbon atoms, preferably 4 to 8 carbon atoms. In the compounds (i) to (iii), the term "lower" indicates that it has 1 to 3 carbon atoms.

The compounds represented by the formulae I-I, I-a and II-I may be in the form of a salt thereof. The salts which can be formed include, for example, hydrochlorides, bromates, nitrates, sulfates, phosphates, toluenesulfonates and the like.

The alkyl and acyl groups represented by $R_5$ and $R_6$ in the formulae II and II-I are particularly preferably those free from aryl groups.

In the formulae I, II, I-I, I-a and II-I, particularly preferred $L_1$ and $L_2$ are alkylene groups having 4 to 8 carbon atoms.

The description will be made on the formula III.

The alkyl groups represented by $R_7$ and $R_8$ in the formula III are those having 1 to 18 carbon atoms (such as methyl, ethyl, butyl, octyl, dodecyl and octadecyl groups), preferably those having 1 to 8 carbon atoms (such as methyl, ethyl, butyl and octyl groups). The alkylcarbonyl groups are those having 1 to 18 carbon atoms (such as acetyl, butanoyl, octanoyl, tetradecanoyl and octadecanoyl groups), preferably those having 1 to 8 carbon atoms (such as acetyl, butanoyl and octanoyl groups). The alkyl groups contained in these groups may be linear, branched or cyclic, and they may further have a substituent. The most preferred alkyl groups are linear alkyl groups. The alkyl groups having a substituent are preferably those having an aryl group, particularly phenylalkylene groups in which the alkylene group has 1 to 3 carbon atoms.

The halogen atoms represented by $R_9$ and $R_{10}$ in the formula III include fluorine, chlorine, bromine and iodine atoms. Among them, fluorine, chlorine and bromine atoms are preferred. Chlorine atom is particularly preferred. The alkyl groups are those having 1 to 18 carbon atoms (such as methyl, butyl, octyl, dodecyl and octadecyl groups), preferably those having 1 to 8 carbon atoms (such as methyl, ethyl, butyl and octyl groups).

The compounds represented by the formula III may be in the form of a salt thereof. The salts which can be formed include, for example, hydrochlorides, bromates, nitrates, sulfates, phosphates toluenesulfonates and the like.

The particularly preferred compounds of the formula III are those of the following formula III-a:

III-a

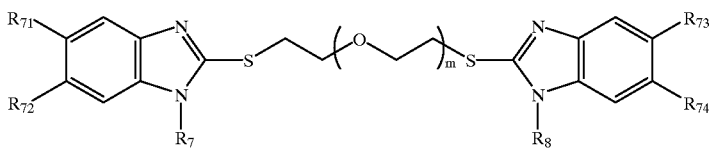

wherein $R_7$ and $R_8$ are as defined above, $R_{71}$ and $R_{72}$ are the same as $R_9$, and $R_{73}$ and $R_{74}$ are the same as $R_{10}$.

In the formula III-a, $R_7$ and $R_8$ are preferably the same as each other.

In the formula III-a, it is preferred that the combination of $R_{71}$ and $R_{72}$ is the same as the combination of $R_{73}$ and $R_{74}$ (namely, $R_{71}=R_{73}$ and $R_{72}=R_{74}$ or $R_{71}=R_{74}$ and $R_{72}=R_{73}$).

The compounds represented by the formulae III-a may be in the form of a salt thereof. The salts which can be formed include, for example, hydrochlorides, bromates, nitrates, sulfates, phosphates and toluenesulfonates.

The alkyl and alkylcarbonyl groups represented by $R_7$ and $R_8$ in the formula III-a are particularly preferably those free from aryl groups as a substituent. Linear alkyl groups and linear alkylcarbonyl groups are more preferred.

Among the compounds of the formula III-a, those of the following groups (i) to (iv) are particularly preferred:

(i) Compounds in which both $R_7$ and $R_8$ represent a hydrogen atom, an alkyl group (particularly unsubstituted linear alkyl group) having 1 to 8 carbon atoms or an alkylcarbonyl group (particularly unsubstituted linear alkylcarbonyl group) having 1 to 8 carbon atoms, $R_{71}$, $R_{72}$, $R_{73}$ and $R_{74}$ each represent a hydrogen, and m is 1.

(ii) Compounds in which both $R_7$ and $R_8$ represent an alkyl group (particularly unsubstituted linear alkyl group) having 1 to 8 carbon atoms or an alkylcarbonyl group (particularly unsubstituted linear alkylcarbonyl group) having 1 to 8 carbon atoms, one or both of $R_{71}$ and $R_{72}$ represent an alkyl group (particularly unsubstituted linear alkyl group) having 1 to 8 carbon atoms or a halogen atom (particularly chlorine atom), and one or both of $R_{73}$ and $R_{74}$ represent an alkyl group (particularly unsubstituted linear alkyl group) having 1 to 8 carbon atoms or a halogen atom (particularly chlorine atom), and m is 1.

(iii) Compounds in which both $R_7$ and $R_8$ represent a hydrogen atom, one or both of $R_{71}$ and $R_{72}$ represent a halogen atom (particularly chlorine atom) or nitro group, preferably $R_{71}$ represents a halogen atom (particularly chlorine atom) or nitro group, and one or both of $R_{73}$ and $R_{74}$ represent a halogen atom (particularly chlorine atom) or nitro group, preferably $R_{73}$ represents a halogen atom (particularly chlorine atom) or nitro group, and m is 1.

(iv) Compounds in which both $R_7$ and $R_8$ represent a hydrogen atom or an alkyl group (particularly unsubstituted linear alkyl group) having 1 to 8 carbon atoms, $R_{71}$, $R_{72}$, $R_{73}$ and $R_{74}$ each a hepresent a hydrogen atom, and m is 2 or 3.

The description will be made on the compounds of the formula IV.

$R_3$, $R_4$, $n_3$, $n_4$ and $L_2$ in the formula IV are as defined in the above formula II and preferred examples of them are also the same as those described above with reference to the formula II. The compounds of the formula IV in which $R_3$ and $R_4$ each represent a hydrogen are also preferred.

The alkyl groups represented by $R_{50}$ and $R_{60}$ in the formula IV are those having 1 to 18 carbon atoms (such as methyl, ethyl, butyl, octyl, dodecyl and octadecyl groups), preferably those having 1 to 8 carbon atoms (such as methyl, ethyl, butyl and octyl groups). They may be either linear or branched. The acyl groups include alkanoyl, arylcarbonyl, alkylsulfonyl, arylsulfonyl, alkoxycarbonyl, sulfamoyl and carbamoyl groups. The alkanoyl groups include those having 1 to 18 carbon atoms (such as acetyl, butanoyl, octanoyl and octadecanoyl groups), preferably those having 1 to 8 carbon atoms (such as acetyl, butanoyl and octanoyl groups). The alkanoyl groups may be linear, branched or cyclic, and the alkyl and aryl groups may further have a substituent. The arylcarbonyl groups are those having 6 to 18 carbon atoms (such as benzoyl and naphthoyl groups) and they may be further substituted. The alkoxycarbonyl groups include those having 1 to 18 carbon atoms (such as methoxycarbonyl, ethoxycarbonyl, octyloxycarbonyl and octadecylcarbonyl groups), preferably those having 1 to 8 carbon atoms (such as methoxycarbonyl, ethoxycarbonyl and octyloxycarbonyl groups). The may be linear, branched or cyclic and may have a substituent.

The alkylsulfonyl groups and arylsulfonyl groups include those having 1 to 18 carbon atoms and those having 6 to 18 carbon atoms, respectively, (such as methanesulfonyl, butanesulfonyl, hexadecanesulfonyl, benzenesulfonyl and naphthalenesulfonyl groups) which may further have a substituent. The alkoxycarbonyl groups include those having 1 to 18 carbonatoms (such as methoxycarbonyl, ethoxycarbonyl, octyloxycarbonyl and tetradecyloxycarbonyl groups), preferably those having 1 to 8 carbon atoms (such as methoxycarbonyl, ethoxycarbonyl and octyloxycarbonyl groups) which may further have a substituent. The sulfamoyl groups include those having 0 to 18 carbon atoms (such as sulfamoyl, methylsulfamoyl, diethysulfamoyl, octylsulfamoyl, hexadecylsulfamoyl and phenylsulfamoyl groups), preferably those having 0 to 8 carbon atoms (such as sulfamoyl, methylsulfamoyl, diethylsulfamoyl and octylsulfamoyl groups) which may further have a substituent. The carbamoyl groups include those having 0 to 18 carbon atoms (such as carbamoyl, methylcarbamoyl, diethylcarbamoyl, octylcarbamoyl, hexadecylcarbamoyl and phenylcarbamoyl groups), preferably those having 0 to 8 carbon atoms (such as methylcarbamoyl, diethylcarbamoyl and octylcarbamoyl groups) which may further have a substituent.

The acyl groups are preferably alkanoyl, arylcarbonyl, alkylsulfonyl, alkoxycarbonyl and carbamoyl groups.

The compounds represented by the formula IV may form a salt. The salts which can be formed by these compounds include, for example, hydrochlorides, bromates, nitrates, sulfates, phosphates, toluenesulfonates and the like.

The particularly preferred compounds of the formula IV are those of the following formula IV-a:

IV-a

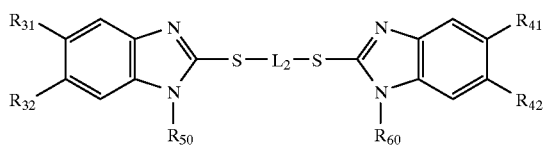

wherein $L_2$, $R_{50}$ and $R_{60}$ are as defined above, $R_{31}$ and $R_{32}$ are the same as $R_3$, and $R_{41}$ and $R_{42}$ are the same as $R_4$.

The preferred substituents in the formula IV are also preferred in the formula IV-a.

In the formula IV-a, $R_{50}$ and $R_{60}$ are preferably the same as each other.

In the formula IV-a, it is further preferred that the combination of $R_{31}$ and $R_{32}$ is the same as the combination of $R_{41}$ and $R_{42}$ (namely, $R_{31}=R_{41}$ and $R_{32}=R_{42}$ or $R_{31}=R_{42}$ and $R_{32}=R_{41}$).

The compounds represented by the formula IV-a may form a salt. The salts which can be formed by these compounds include, for example, hydrochlorides, bromates, nitrates, sulfates, phosphates, toluenesulfonates and the like.

Among the compounds of the formula IV-a, those of the following groups (i) to (v) are particularly preferred from the viewpoint of the pharmacological effect:

(i) Compounds in which all of $R_{31}$, $R_{32}$, $R_{41}$, $R_{42}$, $R_{50}$ and $R_{60}$ each represent a hydrogen, and $L_2$ represents an alkylene group having 4 to 10 carbon atoms, preferably 4 to 8 carbon atoms, namely, $L_2$ is preferably an alkylene-phenylene-alkylene group (the alkylene having desirably 1 to 2 carbon atoms).

(ii) Compounds in which one of $R_{31}$ and $R_{32}$ and one of $R_{41}$ and $R_{42}$ are a hydrogen, and the other is a lower alkyl, halogen (particularly chlorine), nitro or lower acylamino and $R_{50}$ and $R_{60}$ each represent a hydrogen, lower alkyl or lower alkanoyl.

(iii) Compounds in which $R_{31}$, $R_{32}$, $R_{41}$ and $R_{42}$ each represent a halogen (particularly chlorine), and $R_{50}$ and $R_{60}$ each represent a hydrogen.

(iv) Compounds in which $R_{31}$, $R_{32}$, $R_{41}$ and $R_{42}$ each represent a hydrogen, and $R_{50}$ and $R_{60}$ each represent a lower alkanoyl or lower alkyl, and $L_2$ is the same as that in (i).

(v) Compounds in which $R_{31}$, $R_{32}$, $R_{41}$ and $R_{42}$ each represent a halogen (particularly chlorine) or lower alkyl, and $R_{50}$ and $R_{60}$ each represent a lower alkanoyl or lower alkyl.

$L_2$ in the above-described compounds (ii), (iii) and (v) is desirably an alkylene group having 4 to 10 carbon atoms, preferably 4 to 8 carbon atoms. In the compounds (i) to (v), the term "lower" indicates that it has 1 to 3 carbon atoms.

The alkyl and acyl groups represented by $R_{50}$ and $R_{60}$ in the formulae IV and IV-a are particularly preferably those free from aryl groups. They are more preferably a linear alkyl group or linear alkylacyl group.

In the formulae IV and IV-a, particularly preferred $L_2$ is an alkylene group having 4 to 8 carbon atoms.

Examples of typical benzimidazole derivatives of the formulae I to III in the present invention are given below. The numerals (1) to (22) for the compounds of the formula (III) are the same as the numerals for the synthesis examples in Example 2.

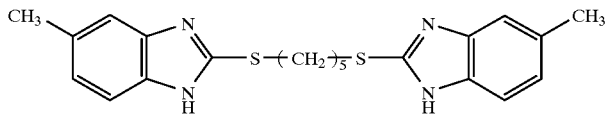

(I-1)

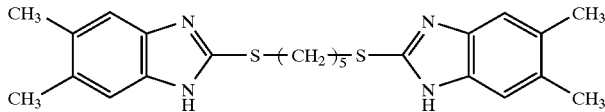

(I-2)

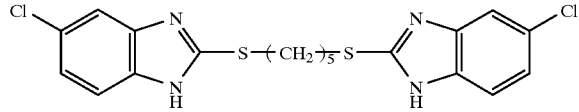

(I-3)

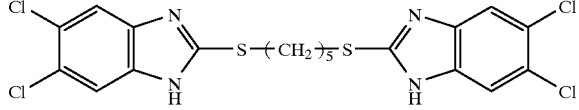

(I-4)

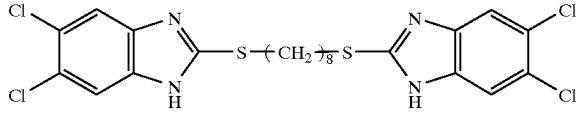

(I-5)

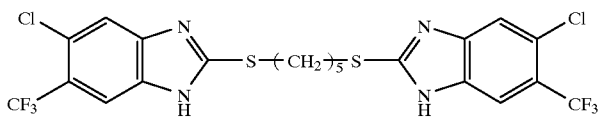
(I-6)
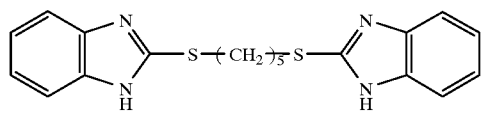
(I-7)
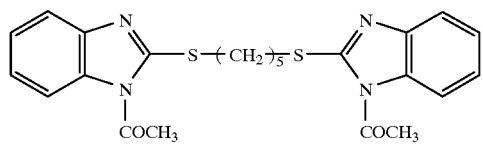
(II-1)
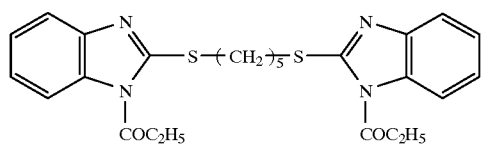
(II-2)
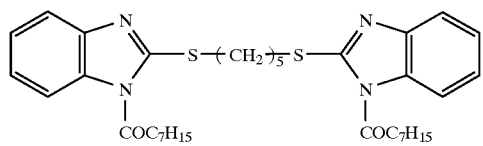
(II-3)
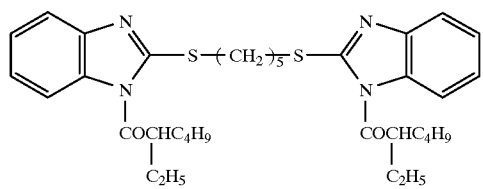
(II-4)
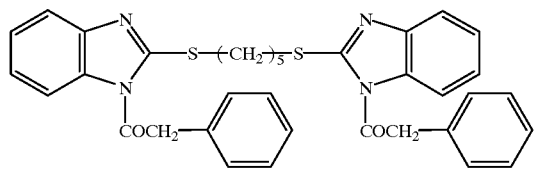
(II-5)
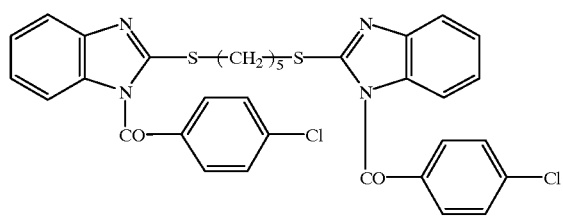
(II-6)
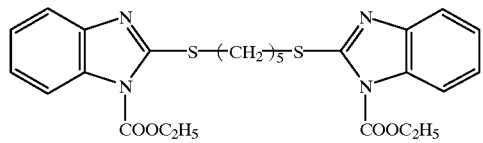
(II-7)

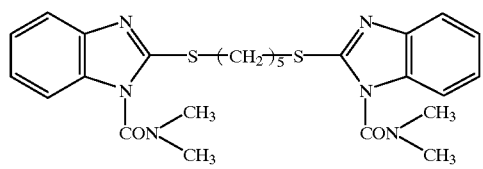 (II-8)
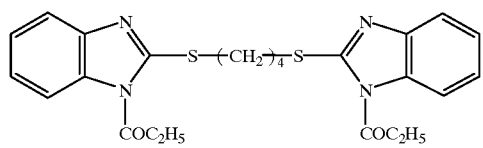 (II-9)
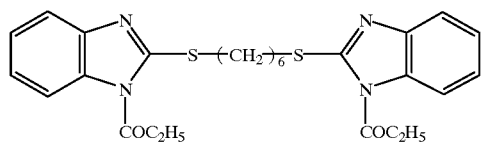 (II-10)
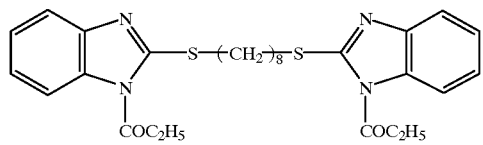 (II-11)
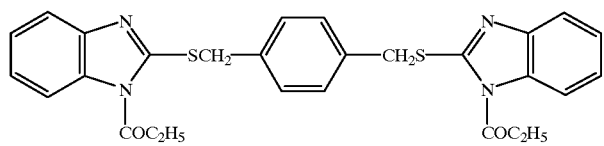 (II-12)
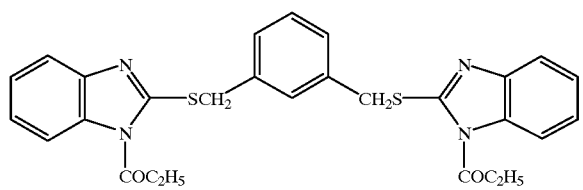 (II-13)
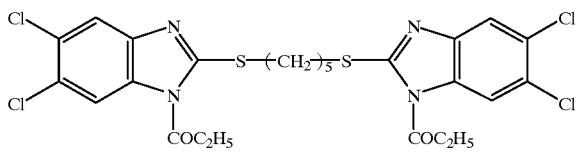 (II-14)
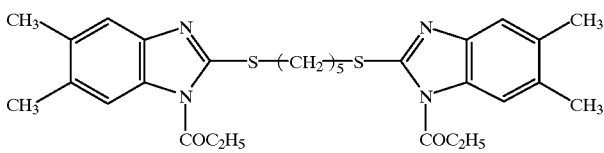 (II-15)
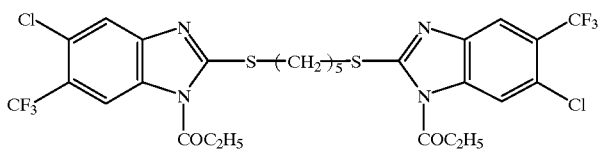 (II-16)

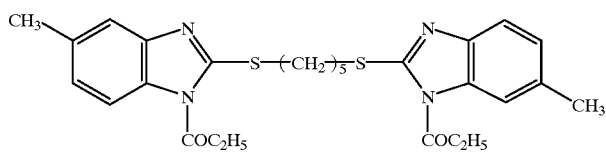
(II-17)
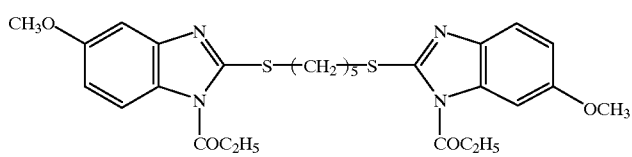
(II-18)
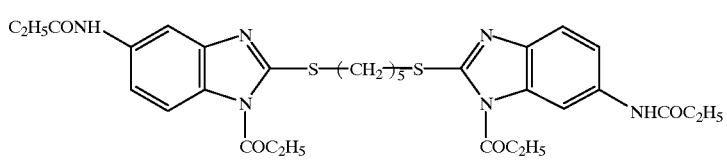
(II-19)
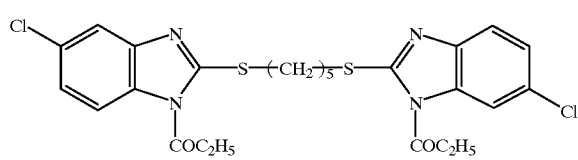
(II-20)
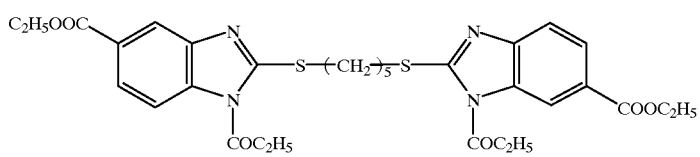
(II-21)
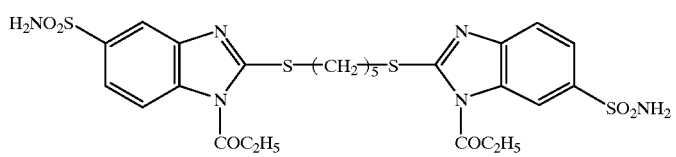
(II-22)
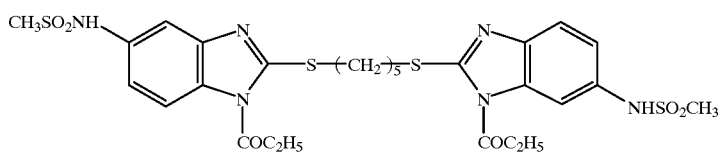
(II-23)
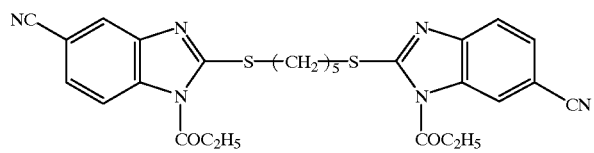
(II-24)
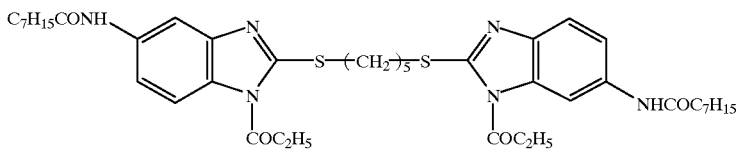
(II-25)

-continued
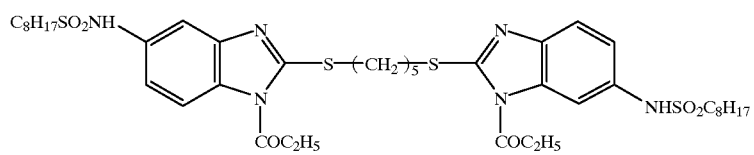
(II-26)
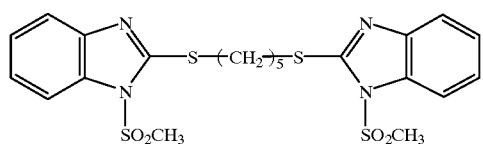
(II-27)
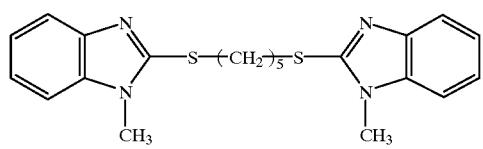
(II-28)
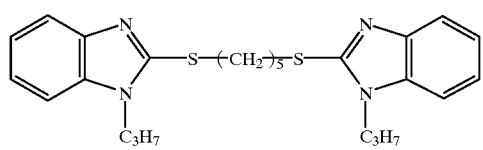
(II-29)
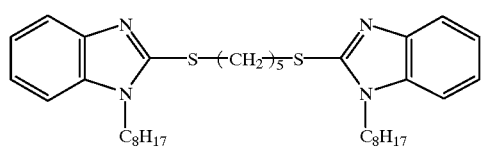
(II-30)
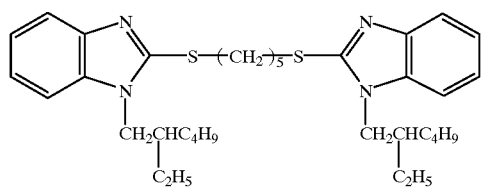
(II-31)
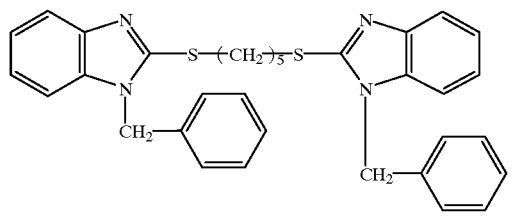
(II-32)
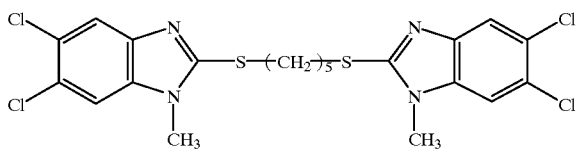
(II-33)
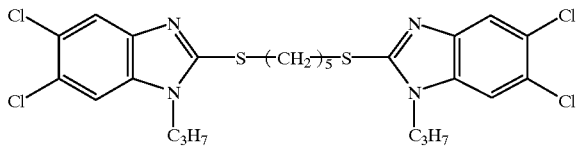
(II-34)

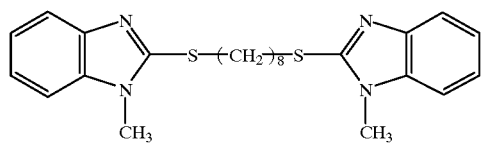
(II-35)
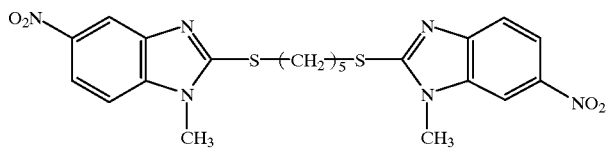
(II-36)
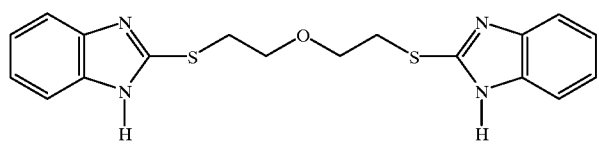
(1)
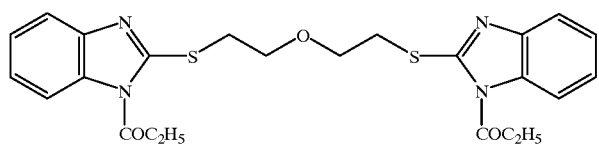
(2)
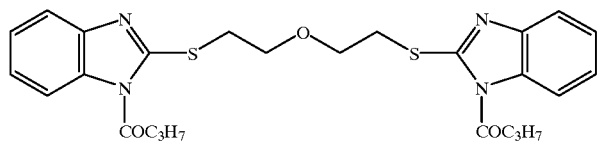
(3)
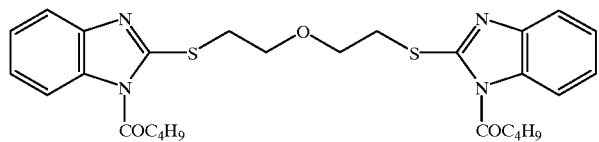
(4)
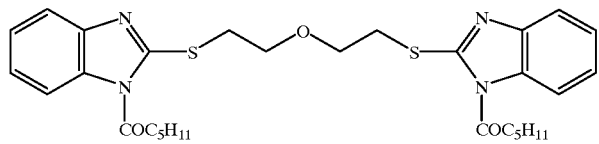
(5)
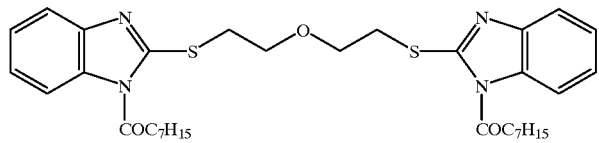
(6)
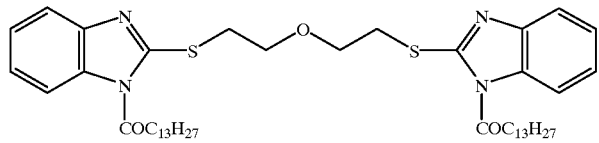
(7)

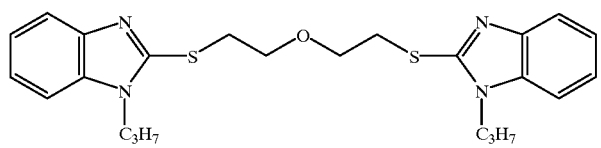
(8)
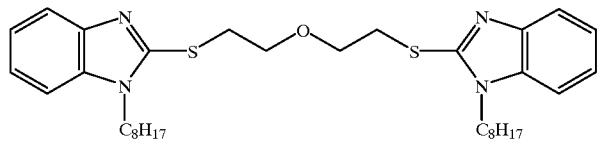
(9)
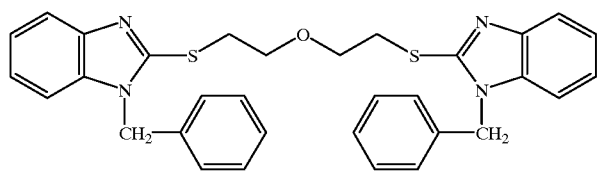
(10)
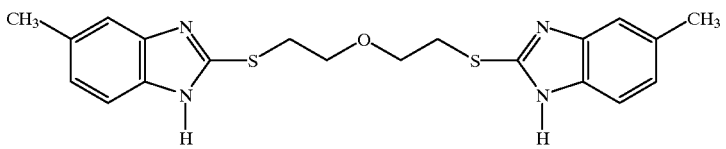
(11)
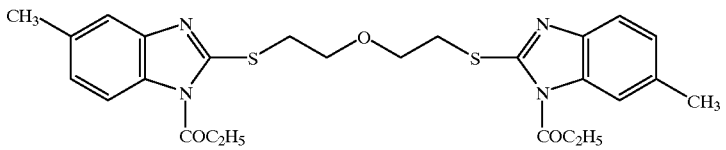
(12)
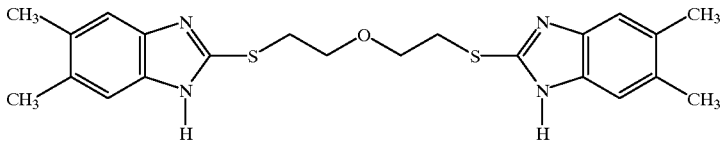
(13)
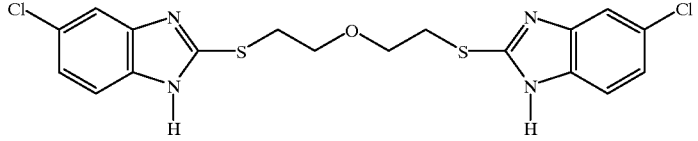
(14)
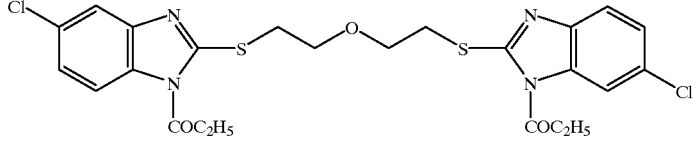
(15)
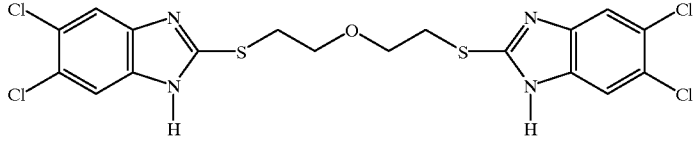
(16)

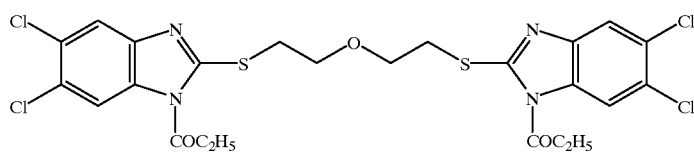
(17)
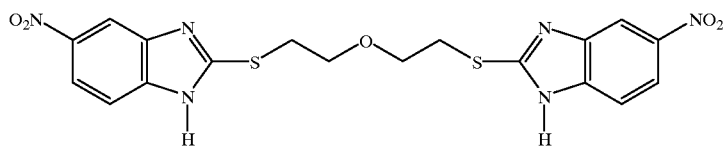
(18)
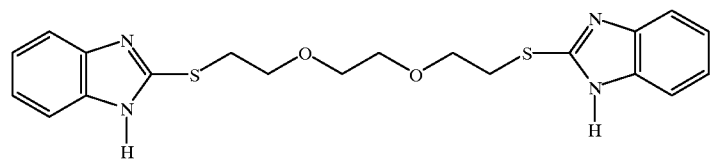
(19)
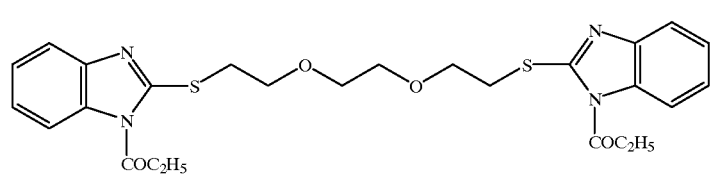
(20)
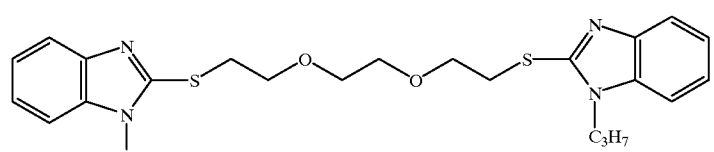
(21)
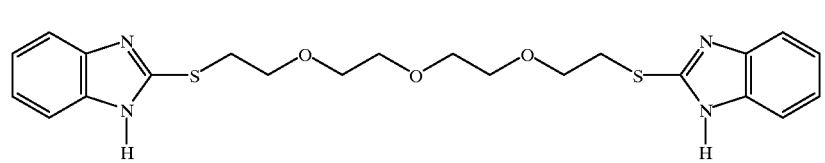
(22)
Examples of the compounds represented by the formula (IV) are as follows:
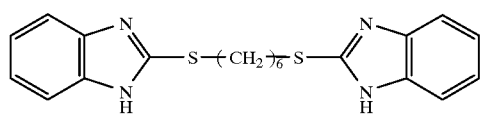
IV-1
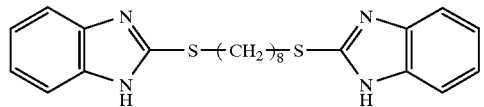
IV-2
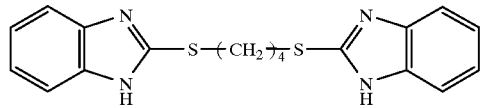
IV-3

-continued
IV-4
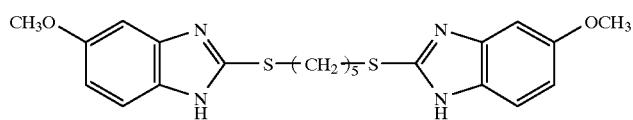
IV-5
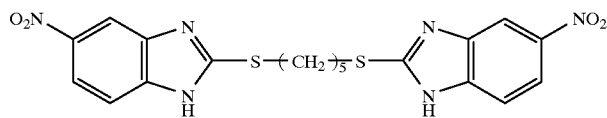
IV-6
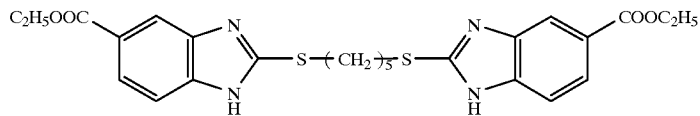
IV-7
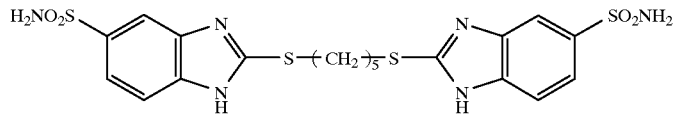
IV-8
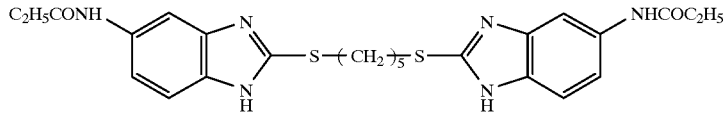
IV-9
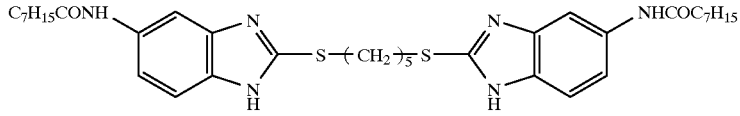
IV-10
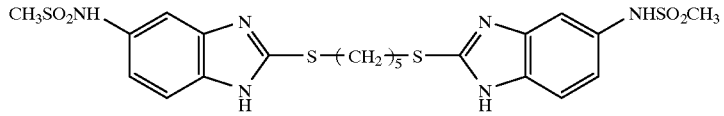
IV-11
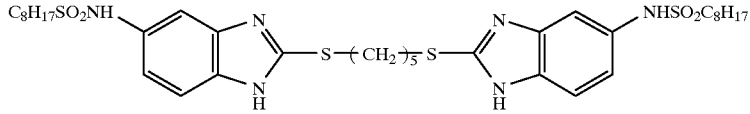
IV-12
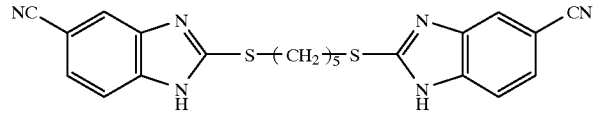
IV-13
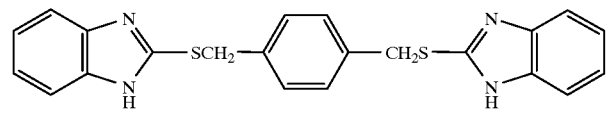
IV-14
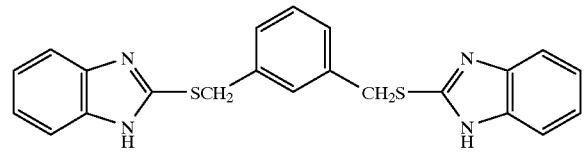
The compounds represented by the formula (IV) include compounds (I-1) to (I-7) and (II-1) to (II-36) in addition to those given above.
2-Mercaptobenzimidazole derivatives represented by the formula I, I-I, I-a, II, II-a or VI can be produced by the following reaction scheme I (formulae 1, 2 and 3):

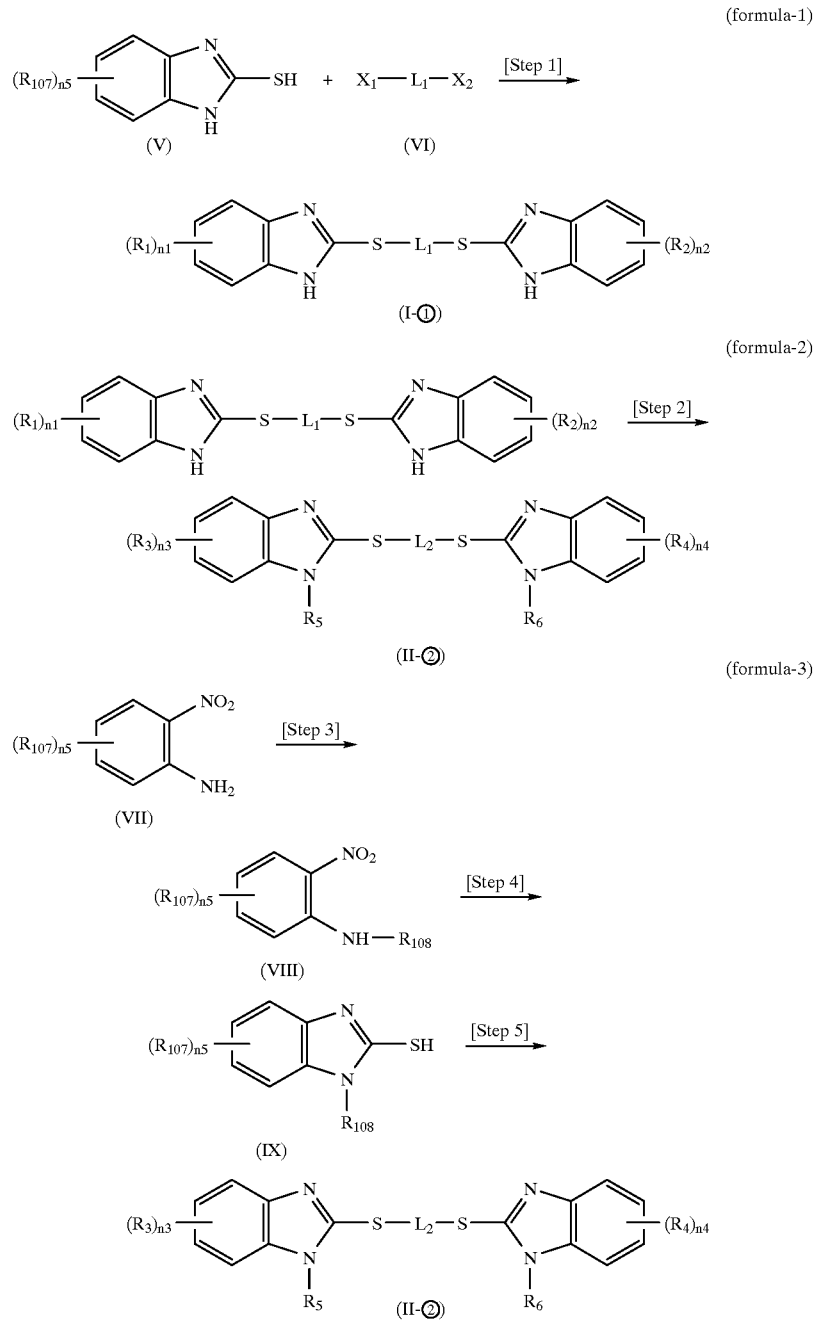

wherein $R_1, R_2, R_3, R_4, R_5, R_6, n_1, n_2, n_3, n_4, L_1$ and $L_2$ are as defined above, $R_{107}$ is the same as $R_1, R_2, R_3$ and $R_4$, $R_{108}$ is the same as $R_5$ and $R_6$, $n_5$ is the same as $n_1, n_2, n_3$ and $n_4$, and $X_1$ and $X_2$ each represent a halogen atom or a group which is split off by the nucleophilic substitution reaction such as a sulfonic ester.

(Formula-1)

[Step 1] Although 2-Mercaptobenzimidazoles (V) used for this reaction are available on the market or known compounds, these compounds can be usually synthesized by a method described in Org. Syn., Col. Vol. 4, p. 569. Compounds (I-①) can be synthesized by reacting a corresponding 2-mercaptobenzimidazole (V) with a bonding group (VI) having two splitting-off groups. Although it is usually desirable to conduct this reaction in the presence of a basic catalyst such as sodium hydroxide, potassium carbonate, triethylamine or sodium ethylate as a deacidifying agent in an ordinary organic solvent [such as ethanol, acetonitrile, acetone, ethyl acetate, DMF (dimethylformamide) or THF (tetrahydrofuran)], this reaction can be also conducted under heating in the absence of any catalyst in an alcohol.

When the basic compound is used, the reaction temperature which varies depending on the substrate and solvent is usually 0 to 150° C., preferably 20 to 100° C. On the other hand, when the reaction is conducted in the absence of the catalyst in an alcohol, the reaction temperature is preferably 50 to 120° C.

The compound (VI) is used in an amount of 0.35 to 0.7 mol, preferably 0.45 to 0.55 mol, per mol of the compound (V), and an insufficient or excess amount thereof is undesirable for inhibiting side reactions in this step.
(Formula-2)

[Step 2] Where the compound (I-①) can be acylated to form a compound (II-①), it can be carried out by reacting the compound (I-①) with a corresponding acid halide in the presence of a basic catalyst (such as potassium carbonate, triethylamine or pyridine) as the deacidifying agent in an ordinary inert solvent [such as acetonitrile, ethyl acetate, THF, DMF, DMAc (dimethylacetamide)]. However, when DMF, DMAc, acetonitrile or the like having a high polarity is used, the basic catalyst is unnecessary.

The amount of the solvent used in this step is preferably 2 to 50 parts per part of the compound (I-①), and that of the acid halide is 1.8 to 2.4 mol per mol of the compound (I-①). Although the reaction can proceed at 30 to 150° C., it is preferably conducted at 50 to 100° C.

When n is 1, an asymmetrically substituted product is preferentially obtained as shown in most Synthesis Examples.

In the alkylation of the compound (I-①) to form the compound (II-①), the former is reacted with an alkyl halide, alkyl tosylate or the like in the presence of a basic catalyst such as sodium hydroxide, potassium carbonate, triethylamine or sodium ethylate as the deacidifying agent in an ordinary organic solvent [such as ethanol, acetonitrile, acetone, ethyl acetate, DMF (dimethylformamide) or THF (tetrahydrofuran)].

The reaction temperature which varies depending on the substrate and solvent is usually 0 to 100° C., preferably 20 to 60° C.

(Formula-3) is a scheme of a production process which can be conducted in place of (formula-1) or (formula-2) when $R_5$ and $R_6$ each represent an alkyl group.

In [step 3] through [step 5], an o-nitroamine compound of the formula (VII) is alkylated by reacting it with an alkyl halide (by, for example, the reaction with a theoretical amount of an alkyl halide in a solvent such as an alcohol, THF or DMF) or by reacting it with an aldehyde under reducing conditions (by, for example, the reaction with an excess amount of an aldehyde, ammonia and hydrogen in the presence of Raney nickel catalyst and sodium acetate as the base in an autoclave). Then the nitro group is reduced (by, for example, the hydrogenation conducted in the presence of vanadium, platinum or Raney nickel as the catalyst in methanol or ethanol, or by the reduction with reduced iron in acetic acid or isopropanol). Thereafter, the product is converted into 2-mercaptobenzimidazole by a method described in Org. Syn., Col. Vol. 4, p. 569 to obtain the corresponding compound (II-②) in the same step as that of (formula 1).

On the other hand, the benzimidazole derivatives of the present invention represented by the formulae III and III-a can be produced by, for example, the following reaction scheme (formula-4 and formula-5):

(formula-4)

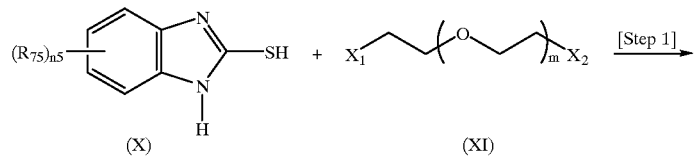

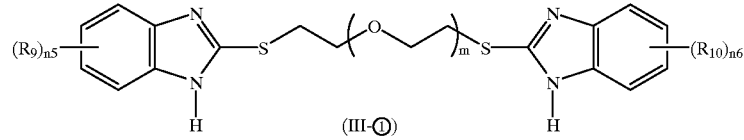

(formula-5)

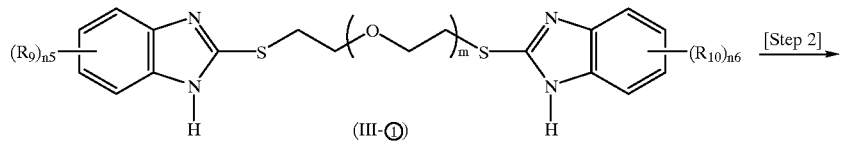

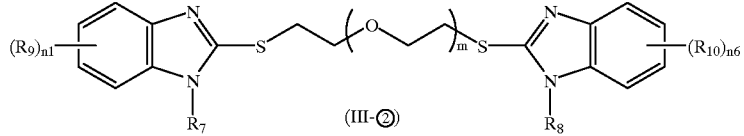

wherein $R_7$, $R_8$, $R_9$, $R_{10}$, $n_5$, $n_6$ and m are as defined above, $R_{75}$ has the same meaning as that of $R_9$ and $R_{10}$, $X_1$ and $X_2$ each represent a halogen atom or a group which is split off by the nucleophilic substitution reaction such as a sulfonic ester.

(Formula-4)

[Step 1] Although 2-Mercaptobenzimidazoles (X) used for this reaction are available on the market or known compounds, these compounds can be generally synthesized by a method described in Org. Syn., Col. Vol. 4, p. 569. Compounds (III-①) can be synthesized by reacting a corresponding 2-mercaptobenzimidazole (X) with a bonding group (XI) having two splitting-off groups. Although it is usually desirable to conduct this reaction in the presence of a basic catalyst such as sodium hydroxide, potassium carbonate, triethylamine or sodium ethylate as a deacidifying agent in an ordinary solvent [such as ethanol, acetonitrile, acetone, ethyl acetate, DMF (dimethylformamide) or THF (tetrahydrofuran)], this reaction can be conducted under heating in the absence of any catalyst in an alcohol or acetonitrile. The bonding groups (XI) having two splitting-off groups usable herein include diethylene glycol di-p-tosylate, triethylene glycol di-p-tosylate, tetraethylene glycol di-p-tosylate, 2,2'-diiododiethyl ether, 2,2'-dichlorodiethyl ether and the like.

When the basic compound is used, the reaction temperature which varies depending on the substrate and solvent is usually 0 to 150° C., preferably 20 to 100° C. On the other hand, when the reaction is conducted in the absence of the catalyst in an alcohol or acetonitrile, the reaction temperature is preferably 50 to 120° C.

The compound (XI) is used in an amount of 0.35 to 0.7 mol, preferably 0.45 to 0.55 mol, per mol of the compound (X), and an insufficient or excess amount thereof is undesirable for inhibiting side reactions in this step.
(Formula-5)

[Step 2] Where the compound (III-①) can be acylated to form a compound (III-②), it can be carried out by reacting compound (III-①) with a corresponding acid halide in the presence of a basic catalyst (such as potassium carbonate, triethylamine or pyridine) as the deacidifying agent in an ordinary inert solvent [such as acetonitrile, ethyl acetate, THF, DMF or DMAc (dimethylacetamide)]. However, when DMF, DMAc, acetonitrile or the like having a high polarity is used, the basic catalyst is unnecessary.

The amount of the solvent used in this step is preferably 2 to 50 parts per part of the compound (III-①), and that of the acid halide is 1.8 to 2.4 mol per mol of the compound (III-①). Although the reaction can proceed at 30 to 150° C., it is preferably conducted at 50 to 100° C.

When $n_5$ and $n_6$ are 1, an asymmetrically substituted product is preferentially obtained as shown in most synthesis examples in Example 2.

In the alkylation of the compound (III-①) to form the compound (III-②), the former is reacted with an alkyl halide or alkyl tosylate in the presence of a basic catalyst such as sodium hydroxide, potassium carbonate, triethylamine or sodium ethylate as the deacidifying agent in an ordinary organic solvent [such as ethanol, acetonitrile, acetone, ethyl acetate, DMF (dimethylformamide) or THF (tetrahydrofuran)]. The reaction temperature which varies depending on the substrate and solvent is usually 0 to 100° C., preferably 20 to 60° C.

The antihyperlipemic agent or antiarteriosclerotic agent of the present invention may contain one or more compounds represented by the formula III or IV. Such an agent may be used in combination with a known compatible antihyperlipemic agent or antiarteriosclerotic agent used hitherto in this technical field. The antihyperlipemic agent or antiarteriosclerotic agent used hitherto include Melinamide, Probucol, Mevalotin, etc.

The medicine of the present invention is administered orally, by injection (mainly intramuscular, intravenous or subcutaneous injection) or the like, and it is prepared in a dosage form suitable for the medication. The medicine is usable in the form of an intravenous preparation such as tablets, powder, granules, capsules, syrup, emulsion, suspension or solution, or of an injection. A carrier or diluent suitable for the dosage form and also a suitable physiologically active substance are usable for the preparation.

Examples of preferred medical carriers and diluents for the medicines usable in combination with the compound of the formula III or IV include glucose; saccharose; lactose; ethyl alcohol; glycerol; mannitol; sorbitol; pentaerythritol; diethylene glycol, triethylene glycol, ethylene glycol, propylene glycol, dipropylene glycol, polyethylene glycol 400 and other polyethylene glycols; mono-, di- and triglycerides of saturated fatty acids such as glyceryl trilaurate, glyceryl monostearate, glyceryl tristearate and glyceryl distearate; pectin; starch; corn starch; alginic acid; xylose; talc; lycopodium spores; oils and fats such as olive oil, peanut oil, castor oil, corn oil, wheat malt oil, sesame oil, cotton seed oil, sunflower oil and cod liver oil; gelatin, lecithin; silica; cellulose; cellulose derivtives such as methylhydroxypropylcellulose, methylcellulose, hydroxyethylcellulose and carboxymethylcellulose calcium; magnesium salts or calcium salts of fatty acids having 12 to 22 carbon atoms such as calcium stearate, calcium laurate, magnesium oleate, calcium palmitate, calcium behenate and magnesium stearate; cyclodextrins such as α-cyclodextrin, β-cyclodextrin, γ-cyclodextrin, hydroxyethyl-β-cyclodextrin, hydroxypropyl-β-cyclodextrin, dihydroxypropyl-β-cyclodextrin, carboxymethyl-β-cyclodextrin and dimethyl-β-cyclodextrin; emulsifying agents such as esters of a saturated or unsaturated fatty acid having 2 to 22, particularly 10 to 18 carbon atoms, with a monohydric aliphatic alcohol (for example, an alkanol having 1 to 20 carbon atoms) or polyhydric alcohol such as glycol, glycerol, diethylene glycol, pentaerythritol, ethyl alcohol, butyl alcohol or octadecyl alcohol; silicones such as dimethylpolysiloxanes; and pyrogen-free distilled water.

The dosage of the medicine of the present invention, which varies depending on the disease, age, body weight and symptoms of the patient and route of administration, is usually in the range of 0.1 to 500 mg, preferably 0.2 to 100 mg, (in terms of the active ingredient) per kg-body weight/day for adults.

The present invention provides the medicine having excellent effect of decreasing blood cholesterol and inhibiting the foaming of macrophases and only a low toxicity and capable of being administered for a long period of time for exhibiting excellent therapeutic effect against hyperlipemia and arteriosclerosis.

The following Examples will further illustrate the present invention.

EXAMPLE 1

The description will be made on examples of synthesis of the compounds according to the present invention.

(1) Synthesis of 1,5-bis(2-benzimidazoylthio)pentane (compound I-7):

45 g of 2-mercaptobenzimidazole and 36 g of 1,5-dibromopentane were dissolved in 120 ml of ethanol, and the thus-obtained solution was refluxed under stirring on a water bath for 14 hours. After cooling, it was neutralized with 150 ml of 2 N aqueous sodium hydroxide solution. Crystals thus formed were collected by filtration, and then washed with hydrous ethanol and acetonitrile. After drying, 55 g of the intended compound was obtained (yield: 99%).

Melting point: 240 to 242° C.; Elementary analysis for $C_{19}H_{20}N_4S_2$: Calculated: C 61.92; H 5.47; N 15.21 (%); Found: C 61.67; H 5.63; N 14.98 (%)

(2) Synthesis of 1,6-bis(2-benzimidazoylthio)hexane (compound IV-1):

38 g (yield: 99%) of the intended compound was obtained from 30 g of 2-mercaptobenzimidazole and 27 g of 1,6-dibromohexane in the same manner as in (1).

Melting point: 222 to 229° C.; Elementary analysis for $C_{20}H_{22}N_4S_2$: Calculated: C 62.79; H 5.80; N 14.65 (%); Found: C 62.46; H 5.92; N 14.48 (%)

(3) Synthesis of 1,8-bis(2-benzimidazoylthio)octane (compound IV-2):

8.1 g (yield: 99%) of the intended compound was obtained from 8.2 g of 2-mercaptobenzimidazole and 5.5 g of 1,8-dibromooctane in the same manner as in (1).

Melting point: 218 to 222° C.; Elementary analysis for $C_{22}H_{26}N_4S_2$: Calculated: C 64.35; H 6.38; N 13.65 (%); Found: C 64.18; H 6.49; N 13.44 (%)

(4) Synthesis of 1,4-bis(2-benzimidazoylthio)butane (compound IV-3):

5.0 g (yield: 94%) of the intended compound was obtained from 4.5 g of 2-mercaptobenzimidazole and 3.1 g of 1,4-dibromobutane in the same manner as in (1).

Melting point: 274 to 277° C.; Elementary analysis for $C_{18}H_{18}N_4S_2$: Calculated: C 60.98; H 5.12; N 15.81 (%); Found: C 60.77; H 5.36; N 15.70 (%)

(5) Synthesis of 1,5-bis(5-methyl-2-benzimidazoylthio)pentane (compound I-1):

8.1 g (yield: 82%) of the intended compound was obtained from 8.2 g of 2-mercapto-5-methylbenzimidazole and 5.5 g of 1,5-dibromopentane in the same manner as in (1).

Melting point: 161 to 163° C.; Elementary analysis for $C_{21}H_{24}N_4S_2$: Calculated: C 63.60; H 6.10; N 14.13 (%); Found: C 63.42; H 6.02; N 14.29 (%)

(6) Synthesis of 1,5-bis(5-methoxyl-2-benzimidazoylthio)pentane (compound IV-4):

3.8 g (yield: 88%) of the intended compound was obtained from 3.6 g of 2-mercapto-5-methoxylbenzimidazole and 2.2 g of 1,5-dibromopentane in the same manner as in (1).

Melting point: 170 to 172° C.; Elementary analysis for $C_{21}H_{24}N_4O_2S_2$: Calculatec: C 58.85; H 5.64; N 13.08 (%); Found: C 58.69; H 5.49; N 13.12 (%)

(7) Synthesis of 1,5-bis(5-chloro-2-benzimidazoylthio)pentane (compound I-3):

12 g of 5-chloro-2-mercaptobenzimidazole and 7.45 g of 1,5-dibromopentane were dissolved in 200 ml of ethanol, and the thus-obtained solution was refluxed under stirring on a water bath for 12 hours. After cooling, it was neutralized with 35 ml of 2 N aqueous sodium hydroxide solution. 200 ml of water was added to the oily substance thus formed. The aqueous layer was removed by decantation. The oily substance was dispersed in 500 ml of acetonitrile. 60 ml of hydrochloric acid was added to the dispersion, and the resultant mixture was stirred for 2 hours. Crystals thus formed were collected by filtration, and then washed with acetonitrile. After drying, 32 g of the intended compound was obtained in the form of its dihydrochloride (yield: 91%).

Melting point: 182 to 188° C.; Elementary analysis for $C_{19}H_{20}N_4S_2Cl_4$: Calculated: C 44.72; H 3.95; N 10.98 (%); Found: C 44.51; H 3.73; N 10.75 (%)

(8) Synthesis of 1,5-bis(5-nitro-2-benzimidazoylthio)pentane (compound IV-5)

1.0 g (yield: 42%) of the intended compound was obtained from 1.95 g of 5-nitro-2-mercaptobenzimidazole and 1.1 g of 1,5-dibromopentane in the same manner as in (1).

Melting point: ~300° C. (decomposition) Elementary analysis for $C_{19}H_{18}N_6O_4S_2$: Calculated: C 43.82; H 3.96; N 15.72 (%); Found: C 43.66; H 3.82; N 15.56 (%)

(9) Synthesis of 1,5-bis(5-ethoxycarbonyl-2-benzimidazoylthio)pentane (compound IV-6):

2.1 g (yield: 72%) of the intended compound in the form of its dihydrochloride was obtained from 2.24 g of 5-ethoxycarbonyl-2-mercaptobenzimidazole and 1.1 g of 1,5-dibromopentane in the same manner as in (7).

Melting point: 176 to 180° C.; Elementary analysis for $C_{25}H_{30}O_4S_2Cl_2$: Calculated: C 51.28; H 5.16; N 9.57 (%); Found: C 51.03; H 5.06; N 9.39 (%)

(10) Synthesis of 1,5-bis(5-sulfamoyl-2-benzimidazoylthio)pentane (compound IV-7):

2.25 g (yield: 86%) of the intended compound was obtained from 2.3 g of 5-sulfamoyl-2-mercaptobenzimidazole and 1.1 g of 1,5-dibromopentane in the same manner as in (1).

Melting point: 181 to 184° C.; Elementary analysis for $C_{19}H_{22}N_6O_4S_4$: Calculated: C 43.33; H 4.21; N 15.96 (%); Found: C 43.12; H 4.10; N 15.73 (%)

(11) Synthesis of 1,5-bis(5-propanamido-2-benzimidazoylthio)pentane (compound IV-8):

16.5 g of 5-amino-2-mercaptobenzimidazole was suspended in a mixture of 40 ml of dimethylacetamide and 70 ml of acetonitrile. 9.8 g of propionyl chloride was dropped into the suspension at 50° C. After stirring at 50° C. for 2 hours, 50 ml of water was added to the reaction mixture. Crystals formed by :neutralization with 70 ml of 2 N aqueous sodium hydroxide solution were collected by filtration, washed with water and dried to obtain 17 g of 2-mercapto-5-propanamidobenzimidazole (yield: 77%).

3.7 g (yield: 71%) of the intended compound was obtained from 4. 4 g of 2-mercapto-5-prapanamidobenzimidazole and 2.2 g of 1,5-dibromopentane in the same manner as in (1).

Melting point: 160 to 163° C.; Elementary analysis for $C_{25}H_{30}N_6O_2S_2$:

Calculated: C 58.80; H 5.92; N 16.46 (%); Found: C 58.63; H 5. 86; N 16.33 (%)

(12) Synthesis of 1,5-bis(5-octanamido-2-benzimidazoylthio)pentane (compound IV-9):

8.3 g of 5-amino-2-mercaptobenzimidazole was suspended in a mixture of 20 ml of dimethylacetamide and 35 ml of acetonitrile. 8.5 g of octanoyl chloride was dropped into the suspension at 50° C. After stirring at 50° C. for 2 hours, 20 ml of water was added to the reaction mixture. Crystals thus formed were collected by filtration, washed with water and dried to obtain 12.8 g of 2-mercapto-5-octanamidobenzimidazole (yield: 88%).

5.2 g (yield: 80%) of the intended compound was obtained from 2. 9 g of 2-mercapto-5-octanamidobenzimidazole and 1.1 g of 1,5-dibromopentane in the same manner as in (1).

Melting point: 132 to 135° C.; Elementary analysis for $C_{35}H_{50}N_6O_2S_2$: Calculated: C 64.58; H 7.74; N 12.29 (%); Found: C 64.42; H 7.65; N 12.73 (%)

(13) Synthesis of 1,5-bis(5-methanesulfonamido-2-benzimidazoylthio) pentane (compound IV-10):

2.2 g (yield: 80%) of the intended compound was obtained from 2.4 g of 5-methanesulfonamido-2-mercaptobenzimidazole and 1.1 g of 1,5-dibromopentane in the same manner as in (1).

Melting point: 168 to 172° C.; Elementary analysis for $C_{21}H_{26}N_6O_4S_4$: Calculated: C 45.47; H 4.72; N 15.15 (%); Found: C 45.22; H 4.61; N 15.28 (%)

(14) Synthesis of 1,5-bis(5-octanesulfonamido-2-benzimidazoylthio) pentane (compound IV-11):

2.2 g (yield: 80%) of the intended compound was obtained from 3.0 g of 5-octanesulfonamido-2-mercaptobenzimidazole and 1.1 g of 1,5-dibromopentane in the same manner as in (1).

Melting point: 153 to 156° C.; Elementary analysis for $C_{35}H_{52}N_6O_4S_4$: Calculated: C 56.12; H 7.00; N 11.22 (%); Found: C 55.96; H 6.87; N 11.12 (%)

(15) Synthesis of 1,5-bis(5-cyano-2-benzimidazoylthio) pentane (compound IV-12):

1.9 g (yield: 91%) of the intended compound was obtained from 1.8 g of 5-cyano-2-mercaptobenzimidazole and 1.1 g of 1,5-dibromopentane in the same manner as in (1).

Melting point: 172 to 175° C.; Elementary analysis for $C_{21}H_{18}N_6S_2$: Calculated: C 60.26; H 4.34; N 20.08 (%); Found: C 59.99; H 4.17; N 19.93 (%)

(16) Synthesis of 1, 5-bis(5-chloro-6-trifluoromethyl-2-benzimidazoylthio)pentane (compound I-6):

2.1 g (yield: 69%) of the intended compound was obtained from 2.5 g of 5-chloro-6-trifluoromethyl-2-mercaptobenzimidazole and 1.1 g of 1,5-dibromopentane in the same manner as in (1).

Melting point: 159 to 163° C.

(17) Synthesis of 1,5-bis(5,6-dimethyl-2-benzimidazoylthio)pentane (compound I-2):

3.9 g (yield: 93%) of the intended compound was obtained from 3.6 g of 2-mercapto-5,6-dimethylbenzimidazole and 2.5 g of 1,5-dibromopentane in the same manner as in (1).

Melting point: 188 to 191° C.; Elementary analysis for $C_{23}H_{28}N_4S_2$: Calculated: C 65.05; H 6.65; N 13.20 (%); Found: C 65.20; H 6.52; N 13.36 (%)

(18) Synthesis of 1,5-bis(5,6-dichloro-2-benzimidazoylthio) Pentane (compound I-4):

4.6 g (yield: 91%) of the intended compound was obtained from 4.4 g of 2-mercapto-5,6-dichlorobenzimidazole and 2.5 g of 1,5-dibromopentane in the same manner as in (1).

Melting point: 213 to 217° C.; Elementary analysis for $C_{19}H_{16}N_4S_2Cl_4$: Calculated: C 45.07; H 3.19; N 11.07 (%); Found: C 44.89; H 3.17; N 10.93 (%)

(19) Synthesis of 1,8-bis(5,6-dichloro-2-benzimidazoylthio) pentane (compound I-5):

4.9 g (yield: 90%) of the intended compound was obtained from 2.2 g of 2-mercapto-5,6-dichlorobenzimidazole and 1.36 g of 1,8-dibromooctane in the same manner as in (1).

Melting point: 172 to 174° C.; Elementary analysis for $C_{22}H_{22}N_4S_2Cl_4$: Calculated: C 48.18; H 4.04; N 10.22 (%); Found: C 47.97; H 3.93; N 10.03 (%)

(20) Synthesis of 1,4-bis(2-benzimidazoylthiomethyl) benzene (compound IV-13):

3.8 g (yield: 95%) of the intended compound was obtained from 3.0 g of 2-mercapto-benzimidazole and 1.66 g of p-xylylene dichloride in the same manner as in (1).

Melting point: 267 to 270° C.; Elementary analysis for $C_{22}H_{18}N_4S_2$: Calculated: C 65.64; H 4.51; N 13.92 (%); Found: C 65.45; H 4.47; N 13.83 (%)

(21) Synthesis of 1,3-bis(2-benzimidazoylthiomethyl) benzene (compound IV-14):

3.88 g (yield: 97%) of the intended compound was obtained from 3.0 g of 2-mercapto-benzimidazole and 3.0 g of m-xylylene dibromide in the same manner as in (1).

Melting point: 227 to 229° C.; Elementary analysis for $C_{22}H_{18}N_4S_2$: Calculated: C 65.64; H 4.51; N 13.92 (%); Found: C 65.49; H 4.42; N 13.79 (%)

(22) Synthesis of 1,5-bis(1-acetyl-2-benzimidazoylthio) pentane (compound II-1):

0.92 g of 1,5-bis(2-benzimidazoylthio)pentane was suspended in a mixture of 4 ml of dimethylacetamide, 7 ml of acetonitrile and 0.84 ml of triethylamine. 0.4 ml of acetyl chloride was dropped into the suspension at 50° C. After stirring at 50° C. for 2 hours, 10 ml of acetonitrile and 4 ml of water were added to the reaction mixture. Crystals thus formed were collected by filtration, washed with acetonitrile and dried to obtain 1.0 g of the intended compound (yield: 86%).

Melting point: 140 to 142° C. Elementary analysis for $C_{23}H_{24}N_4O_2S_2$: Calculated: C 61.10; H 5.35; N 12.38 (%); Found: C 61.02; H 5.42; N 12.16 (%)

(23) Synthesis of 1,5-bis(1-propionyl-2-benzimidazoylthio) pentane (compound II-2):

0.92 g of 1,5-bis(2-benzimidazoylthio)pentane was suspended in a mixture of 4 ml of dimethylacetamide, 7 ml of acetonitrile and 0.84 ml of triethylamine. 0.48 ml of propionyl chloride was dropped into the suspension at 50° C. After stirring at 50° C. for 2 hours, 10 ml of acetonitrile and 4 ml of water were added to the reaction mixture. Crystals thus formed were collected by filtration, washed with acetonitrile and dried to obtain 0.9 g of the intended compound (yield: 75%).

Melting point: 109 to 111° C.; Elementary analysis for $C_{25}H_{28}N_4O_2S_2$: Calculated: C 62.47; H 5.87; N 11.66 (%); Found: C 62.34; H 5.99; N 11.54 (%)

(24) Synthesis of 1,5-bis(1-octanoyl-2-benzimidazoylthio) pentane (compound II-3):

0.92 g of 1,5-bis(2-benzimidazoylthio)pentane was suspended in a mixture of 4 ml of dimethylacetamide, 8 ml of acetonitrile and 0.84 ml of triethylamine. 0.94 ml of octanoyl chloride was dropped into the suspension at 50° C. After stirring at 50° C. for 4 hours followed by cooling, 10 ml of acetonitrile and 4 ml of water were added to the reaction mixture. Crystals thus formed were collected by filtration, washed with acetonitrile and dried to obtain 1.5 g of the intended compound (yield: 97%).

Melting point: 80 to 82° C. Elementary analysis for $C_{35}H_{48}N_4O_2S_2$: Calculated: C 67.56; H 7.61; N 8.92 (%); Found: C 67.70; H 7.79; N 9.03 (%)

(25) Synthesis of 1,5-bis(1-(2-ethylhexanoyl)-2-benzimidazoylthio) pentane (compound II-4):

0.92 g of 1,5-bis(2-benzimidazoylthio)pentane was suspended in a mixture of 4 ml of dimethylacetamide, 7 ml of acetonitrile and 0.84 ml of triethylamine. 1.15 ml of 2-ethylhexanoyl chloride was dropped into the suspension at 50° C. After stirring at 50° C. for 3 hours, 24 ml of of water was added to the reaction mixture. The oily substance thus formed was extracted with ethyl acetate. After washing with water twide, the organic layer was separated. The solvent was distilled off under reduced pressure. The residue was purified by silica gel column chromatography (silica gel 70 g, solvent: chloroform) to obtain 1.5 g (yield: 97%) of the intended compound as an oily substance. (26) Synthesis of 1,5-bis(1-phenylacetyl-2-benzimidazoylthio)pentane (compound II-5):

0.92 g of 1, 5-bis(2-benzimidazoylthio)pentane was suspended in a mixture of 4 ml of dimethylacetamide, 8 ml of acetonitrile and 0.84 ml of triethylamiiie. 0.73 ml of phenylacetyl chloride was dropped into the suspension at 50° C. After stirring at 50° C. for 2 hours followed by cooling, 10 ml of acetonitrile and 4 ml of water were added to the reaction mixture. Crystals thus formed were collected by filtration, washed with acetonitrile and dried to obtain 0.88 g of the intended compound (yield: 58%).

Melting point: 139 to 140° C.; Elementary analysis for $C_{35}H_{32}N_4O_2S_2$: Calculated: C 69.51; H 5.33; N 9.27 (%); Found: C 69.37; H 5.25; N 9.34 (%)

(27) Synthesis of 1,5-bis(1-(4-chlorobenzoyl)-2-benzimidazoylthio) pentane (compound II-6):

0.92 g of 1,5-bis(2-benzimidazoylthio)pentane was suspended in a mixture of 4 ml of dimethylacetamide, 7 ml of acetonitrile and 0.84 ml of triethylamine. 0.70 ml of 4-chlorobenzoyl chloride was dropped into the suspension at 50° C. After stirring at 50° C. for 2 hours followed by cooling, 10 ml of acetonitrile and 20 ml of water were added to the reaction mixture. The oily product thus formed was collected and then crystallized from acetonitrile+ethanol. The crystals were collected by filtration, washed with acetonitrile and dried to obtain 1.28 g of the intended compound (yield: 79%).

Melting point: 74 to 76° C.; Elementary analysis for $C_{33}H_{26}N_4O_2S_2Cl_2$: Calculated: C 61.39; H 3.82; N 8.68 (%); Found: C 61.24; H 3.93; N 8.53 (%)

(28) Synthesis of 1,5-bis(1-ethoxycarbonyl-2-benzimidazoylthio)pentane (compound II-7):

0.92 g of 1,5-bis(2-benzimidazoylthio)pentane was suspended in a mixture of 4 ml of dimethylacetamide, 7 ml of acetonitrile and 0.84 ml of triethylamine. 0.71 ml of ethyl chlorocarbonate was dropped into the suspension at 50° C. After stirring at 50° C. for 2 hours followed by cooling, 10 ml of acetonitrile and 4 ml of water were added to the reaction mixture. The crystals thus formed were collected by filtration, washed with acetonitrile and dried to obtain 1.3 g of the intended compound (yield: 100%).

Melting point: 72 to 74° C.; Elementary analysis for $C_{25}H_{28}N_4O_4S_2$: Calculated: C 58.57; H 5.51; N 10.93 (%); Found: C 58.43; H 5.62; N 11.14 (%)

(29) Synthesis of 1,5-bis(1-dimethylcarbamoyl-2-benzimidazoylthio) pentane (compound II-8):

0.92 g of 1,5-bis(2-benzimidazoylthio)pentane was suspended in a mixture of 4 ml of dimethylacetamide, 7 ml of acetonitrile and 0.84 ml of triethylamine. 0.51 ml of dimethylcarbamoyl chloride was dropped into the suspension at 50° C. After stirring at 50° C. for 3 hours, 20 ml of water was added Lo the reaction mixture. The oily substance thus formed was extracted with ethyl acetate. After washing with water, the solvent was distilled off under reduced pressure, and the residue was crystallized from hot acetonitrile. The crystals thus formed were collected by filtration, washed with acetonitrile and dried to obtain 0.4 g of the intended compound (yield: 31%).

Melting point: 245 to 247° C.; Elementary analysis for $C_{25}H_{30}N_6O_2S_2$: Calculated: C 58.80; H 5.92; N 16.46 (%); Found: C 58.74; H 5.89; N 16.54 (%)

(30) Synthesis of 1,4-bis(1-propionyl-2-benzimidazoylthio) butane (compound II-9):

0.36 g of 1,4-bis(2-benzimidazoylthio)butane was suspended in a mixture of 2 ml of dimethylacetamide, 4 ml of acetonitrile and 0.35 ml of triethylamine. 0.2 ml of propionyl chloride was dropped into the suspension at 50° C. After stirring at 50° C. for 2 hours followed by cooling, 5 ml of acetonitrile and 2 ml of water were added to the reaction mixture. The crystals thus formed were collected by filtration, washed with acetonitrile and dried to obtain 0.36 g of the intended compound (yield: 77%).

Melting point: 126 to 129° C.; Elementary analysis for $C_{24}H_{26}N_4O_2S_2$: Calculated: C 61.77; H 5.62; N 12.01 (%); Found: C 61.54; H 5.49; N 11.84 (%)

(31) Synthesis of 1,6-bis(1-propionyl-2-benzimidazoylthio) hexane (compound II-10):

0.38 g of 1,6-bis(2-benzimidazoylthio)hexane was suspended in a mixture of 2 ml of dimethylacetamide, 4 ml of acetonitrile and 0.35 ml of triethylamine. 0.2 ml of propionyl chloride was dropped into the suspension at 50° C. After stirring at 50° C. for 2 hours followed by cooling, 5 ml of acetonitrile and 2 ml of water were added to the reaction mixture. The crystals thus formed were collected by filtration, washed with acetonitrile and dried to obtain 0.34 g of the intended compound (yield: 69%).

Melting point: 98 to 101° C.; Elementary analysis for $C_{26}H_{30}N_4O_2S_2$: Calculated: C 63.13; H 6.11; N 11.32 (%); Found: C 63.33; H 5.98; N 11.44 (%)

(32) Synthesis of 1,8-bis(1-propionyl-2-benzimidazoylthio)octane (compound II-11):

0.62 g of 1,8-bis(2-benzimidazoylthio)octane was suspended in a mixture of 3 ml of dimethyl.acetamide, 5 ml of acetonitrile and 0.55 ml of triethylamine. 0.29 ml of propionyl chloride was dropped into the suspension at 50° C. After stirring at 50° C. for 2 hours followed by cooling, 7 ml of acetonitrile and 5 ml of water were added to the reaction mixture. The crystals thus formed were collected by filtration, washed with acetonitrile and dried to obtain 0.60 g of the intended compound (yield: 77%).

Melting point: 93 to 94° C.; Elementary analysis for $C_{28}H_{34}N_4O_2S_2$: Calculated: C 64.33; H 6.56; N 10.72 (%); Found: C 64.21; H 6.48; N 10.64 (%)

(33) Synthesis of 1,4-bis(1-propionyl-2-benzimidazoylthiomethyl)benzene (compound II-12):

0.4 g of 1,4-bis(2-benzimidazoylthiomethyl)benzene was suspended in a mixture of 2 ml of dimethylacetamide, 4 ml of acetonitrile and 0.34 ml of triethylamine. 0.2 ml of propionyl chloride was dropped into the suspension at 50° C. After stirring at 50° C. for 2 hours followed by cooling, 5 ml of acetonitrile and 2 ml of water were added to the reaction mixture. The crystals thus formed were collected by filtration, washed with acetonitrile and dried to obtain 0.42 g of the intended compound (yield: 92%).

Melting point: 220 to 223° C.; Elementary analysis for $C_{28}H_{26}N_4O_2S_2$: Calculated: C 65.34; H 5.09; N 10.88 (%); Found: C 65.15; H 4.98; N 10.62 (%)

(34) Synthesis of 1,3-bis(1-propionyl-2-benzimidazoylthiomethyl)benzene (compound II-13):

0.4 g of 1,3-bis(2-benzimidazoylthiomethyl)benzene was suspended in a mixture of 2 ml of dimethylacetamide, 4 ml of acetonitrile and 0.34 ml of triethylamine. 0.2 ml of propionyl chloride was dropped into the suspension at 50° C. After stirring at 50° C. for 2 hours followed by cooling, 5 ml of acetonitrile and 2 ml of water were added to the reaction mixture. The crystals thus formed were collected by filtration, washed with acetonitrile and dried to obtain 0.45 g of the intended compound (yield: 99%).

Melting point: 193 to 195° C.; Elementary analysis for $C_{28}H_{26}N_4O_2S_2$: Calculated: C 65.34; H 5.09; N 10.88 (%); Found: C 65.41; H 5.12; N 10.73 (%)

(35) Synthesis of 1,5-bis(5.6-dichloro-1-propionyl-2-benzimidazoylthio) pentane (compound II-14):

0.6 g of 1,5-bis(5,6-dichloro-2-benzimidazoylthio) pentane was suspended in a mixture of 2.5 ml of dimethylacetamide, 5 ml of acetonitrile and 0.44 ml of triethylamine. 0.23 ml of propionyl chloride was dropped into the suspension at 50° C. After stirring at 50 ° C. for 4 hours followed by cooling, 7 ml of acetonitrile and 3 ml of water were added to the reaction mixture. The crystals thus formed were collected by filtration, washed with acetonitrile and dried to obtain 0.6 g of the intended compound (yield: 95%).

Melting point: 136 to 138° C.; Elementary analysis for $C_{25}H_{24}N_4O_2S_2Cl_4$: Calculated: C 48.55; H 3.91; N 9.06 (%); Found: C 48.37; H 3.82; N 8.91 (%)

(36) Synthesis of 1,5-bis(5,6-dimethyl-1-propionyl-2-benzimidazoylthio) pentane (compound II-15):

0.64 g of 1,5-bis(5,6-dimethyl-2-benzimidazoylthio) pentane was suspended in a mixture of 3 ml of d imethylacetamide, 5 ml of acetonitrile and 0.5 ml of triethylamine. 0.29 ml of propionyl chloride was dropped into the suspension at 50° C. After stirring at 50° C. for 3 hours followed by cooling, 7 ml of acetonitrile and 3 ml of water were added to the reaction mixture. The crystals thus formed were collected by filtration, washed with acetonitrile and dried to obtain 0.65 g of the intended compound (yield: 81%).

Melting point: 143 to 144° C., Elementary analysis for $C_{29}H_{36}N_4O_2S_2$: Calculated: C 64.89; H 6.76; N 10.44 (%); Found: C 64.98; 11 6.81; N 10.28 (%)

(37) Synthesis of 1-(5-chloro-1-propionyl-6-trifluoromethyl-2-benzimidazoylthio)-5-(6-chloro-1-propionyl-5-trifluoromethyl-2-benzimidazoylthio)pentane (compound II-16):

0.57 g of 1,5-bis(5-chloro-6-trifluoromethyl-2-benzimidazoylthio)pentane was suspended in a mixture of 2 ml of dimethylacetamide, 4 ml of acetonitrile and 0.34 ml of triethylamine. 0.2 ml of propionyl chloride was dropped into the suspension at 50° C. After stirring at 50° C. for 3 hours followed by cooling, 5 ml of acetonitrile and 3 ml of water were added to the reaction mixture. The crystals thus formed were collected by filtration, washed with acetonitrile and dried to obtain 0.55 g of the intended compound (yield: 80%).

Melting point: 111 to 114° C.

(38) Synthesis of 1-(5-methyl-1-propionyl-2-benzimidazoylthio)-5-(6-methyl-1-propionyl-2-benzimidazoylthio)pentane (compound II-17):

0.59 g of 1,5-bis(5-methyl-2-benzimidazoylthio)pentane was suspended in a mixture of 3.5 ml of dimethylacetamide, 7 ml of acetonitrile and 0.5 ml of triethylamine. 0.29 ml of propionyl chloride was dropped into the suspension at 50° C. After stirring at 50° C. for 1.5 hours followed by cooling, 7 ml of acetonitrile and 3 ml of water were added to the reaction mixture. The crystals thus formed were collected by filtration, washed with acetonitrile and dried to obtain 0.60 g of the intended compound (yield: 79%).

Melting point: 105 to 108° C.; Elementary analysis for $C_{27}H_{32}N_4O_2S_2$: Calculated: C 63.75; H 6.34; N 11.06 (%); Found: C 63.61; H 6.22; N 10.89 (%)

(39) Synthesis of 1-(5-methoxyl-1-propionyl-2-benzimidazoylthio)-5-(6-methoxyl-1-propionyl-2-benzimidazoylthio)pentane (compound II-18):

0.64 g of 1,5-bis(5-methoxyl-2-benzimidazoylthio)pentane was suspended in a mixture of 3.5 ml of dimethylacetamide, 7 ml of acetonitrile and 0.5 ml of triethylamine. 0.29 ml of propionyl chloride was dropped into the suspension at 50° C. After stirring at 50° C. for 1.5 hours followed by cooling, 10 ml of water was added to the reaction mixture. The oily product thus formed was extracted with ethyl acetate. The extract was washed with water and then the solvent was distilled off under reduced pressure. The residue was crystallized from acetonitrile The crystals thus obtained were collected by filtration, washed with acetonitrile and dried to obtain 0.52 g of the intended compound (yield: 64%).

Melting point: 103 to 106° C.; Elementary analysis for $C_{27}H_{32}N_4O_4S_2$: Calculated: C 59.97; H 5.97; N 10.36 (%); Found: C 59.69; H 5.84; N 10.23 (%)

(40) Synthesis of 1-(5-propanamido-1-propionyl-2-benzimidazoylthio)-5-(6-propanamido-1-propionyl-2-benzimidazoylthio)pentane (compound II-19):

0.6 g of 1,5-bis(5-propanamido-2-benzimidazoylthio) pentane was suspended in a mixture of 3 ml of dimethylacetamide, 6 ml of acetonitrile and 0.6 ml of triethylamine. 0.33 ml of propionyl chloride was dropped into the suspension at 50° C. After stirring at 50° C. for 1 hour followed by cooling, 5 ml of acetonitrile and 5 ml of water were added to the reaction mixture. The crystals thus obtained were collected by filtration, washed with acetonitrile and dried to obtain 0.58 g of the intended compound (yield: 89%).

Melting point: 109 to 112° C.; Elementary analysis for $C_{31}H_{38}N_6O_4S_2$: Calculated: C 59.78; H 6.15; N 13.50 (%); Found: C 59.66; H 6.09; N 13.21 (%)

(41) Synthesis of 1-(5-chloro-1-propionyl-2-benzimidazoylthio)-5-(6-chloro-1-propionyl-2-benzimidazoylthio)pentane (compound II-20):

0.51 g of 1,5-bis(5-chloro-2-benzimidazoylthio)pentane dihydrochloride was suspended in a mixture of 3 ml of dimethylacetamide, 6 ml of acetonitrile and 0.65 ml of triethylamine. 0.2 ml of propionyl chloride was dropped into the suspension at 50° C. After stirring at 50° C. for 1.5 hour followed by cooling, 7 ml of acetonitrile and 3 ml of water were added to the reaction mixture. The crystals thus obtained were collected by filtration, washed with acetonitrile and dried to obtain 0.4 g of the intended compound (yield: 81%).

Melting point: 95 to 98° C.; Elementary analysis for $C_{25}H_{26}N_4O_2S_2Cl_2$: Calculated: C 54.39; H 4.77; N 10.20 (%); Found: C 54.18; H 4.62; N 10.04 (%)

(42) Synthesis of 1-(5-ethoxycarbonyl-1-propionyl-2-benzimidazoylthio)-5-(6-ethoxycarbonyl-1-propionyl-2-benzimidazoylthio)pentane (compound II-21):

0.58 g of 1,5-bis(5-ethoxycarbonyl-2-benzimidazoylthio) pentane dihydrochloride was suspended in a mixture of 3 ml of dimethylacetamide, 6 ml of acetonitrile and 0.65 ml of triethylamine. 0.2 ml of propionyl chloride was dropped into the suspension at 50° C. After stirring at 50° C. for 2 hours followed by cooling, 7 ml of acetonitrile and 3 ml of water were added to the reaction mixture. The crystals thus obtained were collected by filtration, washed with acetonitrile and dried to obtain 0.52 g of the intended compound (yield: 83%).

Melting point: 83 to 86° C.; Elementary analysis for $C_{31}H_{36}N_4O_6S_2$: Calculated: C 59.59; H 5.81; N 8.97 (%); Found: C 59.42; H 5.79; N 8.81 (%)

(43) Synthesis of 1-(1-propionyl-5-sulfamoyl-2-benzimidazoylthio)-5-(1-propionyl-6-sulfamoyl-2-benzimidazoylthio)pentane (compound II-22):

0.52 g of 1,5-bis(5-sulfamoyl-2-benzimidazoylthio) pentane was suspended in a mixture of 3 ml of dimethylacetamide, 6 ml of acetonitrile and 0.33 ml of triethylamine. 0.2 ml of propionyl chloride was dropped into the suspension at 50° C. After stirring at 50° C. for 1.5 hour followed by cooling, 7 ml of acetonitrile and 3 ml of water were added to the reaction mixture. The crystals thus obtained were collected by filtration, washed with acetonitrile and dried to obtain 0.56 g of the intended compound (yield: 88%).

Melting point: 141 to 146° C.; Elementary analysis for $C_{25}H_{30}N_6O_6S_4$: Calculated: C 47.00; H 4.73; N 13.16 (%); Found: C 46.86; H 4.68; N 13.01 (%)

(44) Synthesis of 1-(5-methanesulfonamido-1-propionyl-2-benzimidazoylthio)-5-(6-methanesulfonamido-1-propionyl-2-benzimidazoylthio)pentane (compound II-23):

0.55 g of 1,5-bis(5-methanesulfonamido-2-benzimidazoylthio) pentane was suspended in a mixture of 3 ml of dimethylacetamide, 6 ml of acetonitrile and 0.33 ml of triethylamine. 0.2 ml of propionyl chloride was dropped into tine suspension at 50° C. After stirring at 50° C. for 2 hours followed by cooling, 7 ml of acetonitrile and 3 ml of water were added to the reaction mixture. The crystals thus obtained were collected by filtration, washed with acetonitrile and dried to obtain 0.58 g of the intended compound (yield: 87%).

(45) Synthesis of 1-(5-cyano-1-propionyl-2-benzimidazoylthio)-5-(6-cyano-1-propionyl-2-benzimidazoylthio)pentane (compound II-24):

0.42 g of 1,5-bis(5-cyano-2-benzimidazoylthio)pentane was suspended in a mixture of 3 ml of dimethylacetamide, 6 ml of acetonitrile and 0.33 ml of triethylamine. 0.2 ml of propionyl chloride was dropped into the suspension at 50° C. After stirring at 50° C. for 2 hours followed by cooling, 7 ml of acetonitrile and 3 ml of water were added to the reaction mixture. The crystals thus obtained were collected by filtration, washed with acetonitrile and dried to obtain 0.42 g of the intended compound (yield: 79%).

Melting point: 128 to 131° C.; Elementary analysis for $C_{27}H_{26}N_6O_2S_2$: Calculated: C 61.11; H 4.94; N 15.84 (%); Found: C 60.97; H 4.87; N 15.68 (%)

(46) Synthesis of 1-(5-octanamido-1-propionyl-2-benzimidazoylthio)-5-(6-octanamido-1-propionyl-2-benzimidazoylthio)pentane (compound II-25):

0.65 g of 1,5-bis(5-octanamido-2-benzimidazoylthio)pentane was suspended in a mixture of 3 ml of dimethylacetamide, 6 ml of acetonitrile and 0.6 ml of triethylamine. 0.33 ml of propionyl chloride was dropped into the suspension at 50° C. After stirring at 50° C. for 1.25 hour followed by cooling, 5 ml of acetonitrile and 5 ml of water were added to the reaction mixture. The crystals thus obtained were collected by filtration, washed with acetonitrile and dried to obtain 0.65 g of the intended compound (yield: 87%).

Melting point: 122 to 126° C.; Elementary analysis for $C_{41}H_{58}N_6O_4S_2$: Calculated: C 64.53; H 7.77; N 11.02 (%); Found: C 64.33; H 7.68; N 11.08 (%)

(47) Synthesis of 1-(5-octanesulfonamido 1-propionyl-2-benzimidazoylthio)-5-(6-octanesulfonamido-1-propionyl-2-benzimidazoylthio)pentane (compound II-26):

0.75 g of 1,5-bis(5-octanesulfonamido-2-benzimidazoylthio) pentane was suspended in a mixture of 3 ml of dimethylacetamide, 6 ml of acetonitrile and 0.33 ml of triethylamine. 0.2 ml of propionyl chloride was dropped into the suspension at 50° C. After stirring at 50° C. for 2 hour followed by cooling, 7 ml of acetonitrile and 3 ml of water were added to the reaction mixture. The crystals thus obtained were collected by filtration, washed with acetonitrile and dried to obtain 0.65 g of the intended compound (yield: 76%).

Melting point: 147 to 150° C.; Elementary analysis for $C_{41}H_{62}N_6O_6S_4$: Calculated: C 57.04; H 7.24; N 9.74 (%); Found: C 57.21; H 7.08; N 9.63 (%)

(48) Synthesis of 1,5-bis(1-methanesulfonyl-2-benzimidazoylthio)pentane (compound II-27):

0.74 g of 1,5-bis(2-benzimidazoylthio)pentane was suspended in a mixture of 4 ml of dimethylacetamide, 7 ml of acetonitrile and 0.67 ml of triethylamine. 0.35 ml of methanesulfonyl chloride was dropped into the suspension at 15° C. After stirring at 20° C. for 12 hours followed by cooling, 10 ml of acetonitrile and 4 ml of water were added to the reaction mixture. The crystals thus obtained were collected by filtration, washed with acetonitrile and dried to obtain 0.78 g of the intended compound (yield: 74%).

Melting point: 140 to 142° C.; Elementary analysis for $C_{21}H_{24}N_4O_4S_4$: Calculated: C 48.07; H 4.61; N 10.68 (%); Found: C 47.86; H 4.47; N 10.56 (%)

(49) Synthesis of 1,5-bis(1-methyl-2-benzimidazoylthio)pentane (compound II-28):

0.92 g of 1,5-bis(2-benzimidazoylthio)pentane, 0.78 g of methyl iodide and 1.04 g of potassium carbonate were added to 7 ml of dimethylformamide, and the resultant mixture was stirred at 30° C. for 6.5 hours. After cooling, 10 ml of water was added to the reaction mixture and then the mixture was neutralized with 2 N hydrochloric acid. The crystals thus obtained were collected by filtration, washed with water and then with acetonitrile and dried to obtain 0.8 g of the intended compound (yield: 81%).

Melting point: 104 to 106° C.; Elementary analysis for $C_{21}H_{24}N_4S_2$: Calculated: C 63.60; H 6.10; N 14.13 (%); Found: C 63.45; H 6.23; N 15.36 (%)

(50) Synthesis of 1,5-bis(1-propyl-2-benzimidazoylthio)pentane (compound II-29):

0.92 g of 1,5-bis(2-benzimidazoylthio)pentane, 0.68 g of propyl bromide and 1.04 g of potassium carbonate were added to 7 ml of dimethylformamide, and the resultant mixture was stirred at 30° C. for 7 hours. After cooling, 10 ml of water was added to the reaction mixture and then the mixture was neutralized with 2 N hydrochloric acid. The oily product thus obtained was extracted with ethyl acetate and washed with water twice. The solvent was distilled off under reduced pressure. After the separation and purification by silica gel column chromatography (silica gel 30 g, solvent: chloroform), 0.8 g of the intended compound was obtained as an oily substance (yield: 71%).

(51) Synthesis of 1,5-bis(l-octyl-2-benzimidazoylthio) pentane (compound II-30):

0.92 g of 1,5-bis(2-benzimidazoylthio)pentane, 1.06 g of octyl bromide and 1.04 g of potassium carbonate were added to 7 ml of dimethylformamide, and the resultant mixture was stirred at 30° C. for 7 hours. After cooling, 10 ml of water was added to the reaction mixture and then the mixture was neutralized with 2 N hydrochloric acid. The oily product thus obtained was extracted with ethyl acetate and washed with water twice. The solvent was distilled off under reduced pressure. After the separation and purification by silica gel column chromatography (silica gel 35 g, solvent: chloroform), 1.38 g of the intended compound was obtained as an oily substance (yield: 93%).

(52) Synthesis of 1,5-bis(1-(2-ethylhexyl)-2-benzimidazoylthio)pentane (compound II-31):

0.74 g of 1,5-bis(2-benzimidazoylthio)pentane, 0.85 g of 2-ethylexyl bromide and 0.83 g of potassium carbonate were added to 7 ml of dimethylformamide, and the resultant mixture was stirred at 50° C. for 18 hours. After cooling, 10 ml of water was added to the reaction mixture and then the mixture was neutralized with 2 N hydrochloric acid. The oily product thus obtained was extracted with ethyl acetate and washed with water twice. The solvent was distilled off under reduced pressure. After the separation and purification by silica gel column chromatography (silica gel 100 g, solvent: chloroform), 0.9 g of the intended compound was obtained as an oily substance (yield: 76%).

(53) Synthesis of 1.5-bis(1-benzyl-2-benzimidazoylthio) pentane (compound II-32):

0.74 g of 1,5-bis(2-benzimidazoylthio)pentane, 0.75 g of benzyl bromide and 0.83 g of potassium carbonate were added to 7 ml of dimethylformamide, and the resultant mixture was stirred at 30° C. for 7 hours. After cooling, 10 ml of water was added to the reaction mixture and then the mixture was neutralized with 2 N hydrochloric acid. The oily product thus obtained was extracted with ethyl acetate and washed with water twice. The solvent was distilled off under reduced pressure, and the product was crystallized from acetonitrile to obtain 0.82 g of the intended crystals (yield: 75%).

Melting point: 111 to 113° C.; Elementary analysis for $C_{33}H_{32}N_4S_2$: Calculated: C 72.22; H 5.88; N 10.21 (%); Found: C 71.95; H 5.76; N 10.07 (%)

(54) Synthesis of 1,5-bis(5,6-dichloro-1-methyl-2-benzimidazoylthio) pentane (compound II-33):

0.60 g of 1,5-bis(5,6-dichloro-2-benzimidazoylthio) pentane, 0.37 g of methyl iodide and 0.50 g of potassium carbonate were added to 5 ml of dimethylformamide, and the resultant mixture was stirred at 30° C. for 8 hours. After cooling, 10 ml of water was added to the reaction mixture and then the mixture was neutralized with 2 N hydrochloric acid. The crystals thus obtained were collected by filtration and washed with acetonitrile to obtain 0.63 g of the intended compound (yield: 98%).

Melting point: 141 to 144° C.; Elementary analysis for $C_{21}H_{20}N_4S_2Cl_4$: Calculated: C 47.20; H 3.77; N 10.49 (%); Found: C 47.08; H 3.69; N 10.33 (%)

(55) Synthesis of 1,5-bis(5,6-dichloro-1-propyl-2-benzimidazoylthio) pentane (compound II-34):

0.60 g of 1,5-bis(5,6-dichloro-2-benzimidazoylthio) pentane, 0.32 g of propyl bromide and 0.50 g of potassium carbonate were added to 5 ml of dimethylformamide, and the resultant mixture was stirred at 30° C. for 24 hours. After cooling, 10 ml of water was added to the reaction mixture and then the mixture was neutralized with 2 N hydrochloric acid. The oily product thus obtained was extracted with ethyl acetate, washed with water and concentrated under reduced pressure. The residue was separated and purified by silica gel column chromatography (silica gel 30 g, solvent: chloroform). 0.55 g of the intended compound was obtained as an oily substance (yield: 78%).

(56) Synthesis of 1,8-bis(1-methyl-2-benzimidazoylthio) octane (compound II-35):

0.62 g of 1,8-bis(2-benzimidazoylthio)octane, 0.47 g of methyl iodide and 0.62 g of potassium carbonate were added to 10 ml of dimethylformamide, and the resultant mixture was stirred at 30° C. for 12 hours. After cooling, 10 ml of water was added to the reaction mixture and then the mixture was neutralized with 2 N hydrochloric acid. The crystals thus obtained were collected by filtration and washed with acetonitrile to obtain 0.58 g of the intended compound (yield: 88%).

Melting point: 117 to 118° C.; Elementary analysis for $C_{24}H_{30}N_4S_2$: Calculated: C 65.71; H 6.89; N 12.78 (%); Found: C 65.54; H 6.71; N 12.56 (%)

(57) Synthesis of 1-(1-methyl-5-nitro-2-benzimidazoylthio)-5-(1-methyl-6-nitro-2-benzimidazoylthio)pentane (compound II-36):

0.32 g of 1,5-bis(5-nitro-benzimidazoylthio)pentane, 0.27 g of methyl iodide and 0.45 g of potassium carbonate were added to 5 ml of dimethylformamide, and the resultant mixture was stirred at 40° C. for 48 hours. 10 ml of water was added to the reaction mixture and then the mixture was neutralized with 2 N hydrochloric acid. The oily product thus obtained was taken by decantation and washed with water.

The residue was crystallized from acetonitrile to obtain 1.6 g of the intended compound (yield: 47%).

Melting point: 158 to 185° C.

The crystals thus obtained was a mixture of the intended compound, a corresponding compound having nitro groups in the 5-position and 5-position and that having nitro groups in the 6-position and 6-position, which compounds could not be easily separated from each other.

EXAMPLE 2

1) Synthesis of Compound (1):

3.0 g of 2-mercaptobenzimidazole and 3.94 g of diethylene glycol di-p-tosylate were suspended in 35 ml of acetonitrile, and the resultant mixture was stirred in nitrogen stream at 50 to 70° C. for 15 hours. After cooling, water was added to the reaction mixture to dissolve the precipitate, and then the mixture was neutralized with 2 N-NaOH. The crystals thus obtained were collected by filtration and washed with acetonitrile to obtain 2.2 g of the intended compound (1) (yield: 59%).

Melting point: 230 to 232° C.; Elementary analysis for $C_{18}H_{18}N_4O_1S_2$: Calculated: C 58.35; H 4.90; N 15.13 (%); Found: C 58.21; H 4.78; N 15.25 (%)

2) Synthesis of Compound (2):

0.68 g of the compound (1) was dissolved in a mixture of 3 ml of DMAc, 5 ml of acetonitrile and 0.8 ml of triethylamine. 0.21 g of propionyl chloride was slowly added to the solution at 50° C. After stirring for 1 hour followed by cooling, 10 ml of acetonitrile and 4 ml of water were added to the resultant mixture. The crystals thus obtained were collected by filtration and washed with acetonitrile to obtain 0.74 g of the intended compound (2) (yield: 84%).

Melting point: 148 to 149° C.; Elementary analysis for $C_{24}H_{26}N_4O_3S_2$: Calculated: C 59.73; H 5.43; N 11.61 (%); Found: C 59.55; H 5.38; N 15.46 (%)

3) Synthesis of Compound (3):

0.42 g (yield: 69%) of the intended compound (3) was obtained from 0.44 g of the compound (1) and 0.31 g of butyroyl chloride in the same manner as that of Synthesis Example 2).

Melting point: 111 to 113° C.; Elementary analysis for $C_{26}H_{30}N_4O_3S_2$: Calculated: C 61.15; H 5.92; N 10.97 (%); Found: C 60.98; H 5.89; N 11.06 (%)

4) Synthesis of Compound (4):

0.46, (yield: 76%) of the intended compound (4) was obtained from 0.44 g of the compound (1) and 0.34 g of caproyl chloride in the same manner as that of Synthesis Example 2).

Melting point: 69 to 71° C.; Elementary analysis for $C_{26}H_{34}N_4O_3S_2$: Calculated: C 62.42; H 6.36; N 10.40 (%); Found: C 62.23; H 6.21; N 10.57 (%)

5) Synthesis of Compound (5):

0.55 g (yield: 82%) of the intended compound (5) was obtained from 0.44 g of the compound (1) and 0.40 g of valeroyl chloride in the same manner as that of Synthesis Example 2).

Melting point: 92 to 93° C.; Elementary analysis for $C_{30}H_{38}N_4O_3S_2$: Calculated: C 63.57; H 6.75; N 9.89 (%); Found: C 63.46; H 6.57; N 9.74 (%)

6) Synthesis of Compound (6):

1.52 g (yield: 94%) g of the intended compound (6) was obtained from 0.96 g of the compound (1) and 1.0 g of capryloyl chloride in the same manner as that of Synthesis Example 2).

Melting point: 88 to 89° C.; Elementary analysis for $C_{34}H_{46}N_4O_3S_2$: Calculated: C 65.56; H 7.44; N 9.00 (%); Found: C 65.43; H 7.27; N 8.84 (%)

7) Synthesis of Compound (7):

1.4 g (yield: 97%) g of the intended compound (7) was obtained from 0.68 g of the compound (1) and 1.1 g of myristoyl chloride in the same manner as that of Synthesis Example 2).

Melting point: 95 to 97° C.; Elementary analysis for $C_{46}H_{70}N_4O_3S_2$: Calculated: C 69.83; H 8.92; N 7.08 (%); Found: C 69.78; H 8.85; N 7.22 (%)

8) Synthesis of Compound (8):

0.68 g of the compound (1) and 1.1 g of potassium carbonate were suspended in 3 ml of DMF. 0.76 g of propyl bromide was added to the suspension, and the resultant mixture was stirred at 35° C. for 8 hours.

After cooling, water was added to the reaction mixture. The oily product thus obtained was extracted with ethyl acetate. The organic layer was washed with water, and the solvent was distilled off under reduced pressure. The residue was purified by silica gel column chromatography (silica gel 30 g, solvent: 5% ethyl acetate/chloroform) to obtain 0.8 g. (yield: 96%) of the intended compound (8) as an oily substance.

9) Synthesis of Compound (9):

0.52 g (yield: 95%) g of the intended compound (9) as an oily substance was obtained from 0.34 g of the compound (1) and 1.13 g of octyl bromide in the same manner as that of Synthesis Example 8).

10) Synthesis of Compound (10):

0.41 g (yield: 88%) g of the intended compound (10) as an oily substance was obtained from 0.34 g of the compound (1) and 0.51 g of benzyl bromide in the same manner as that of Synthesis Example 8).

11) Synthesis of Compound (11):

1.6 g of 5-methyl-2-mercaptobenzimidazole and 2.1 g of diethylene glycol di-p-tosylate were suspended in 20 ml of acetonitrile. The obtained suspension was heated under reflux in nitrogen stream for 28 hours. After cooling, water was added to the reaction mixture to dissolve the precipitate. After the neutralization with 2 N-NaOH, the oily product thus obtained was extracted with ethyl acetate. The organic layer was washed with water, and the solvent was distilled off under reduced pressure. The residue was purified by silica gel column chromatography (silica gel 50 g, solvent: 2% methanol/20% ethyl acetate/chloroform) to obtain 1.6 g (yield: 80%) of the intended compound (11) as an oily substance.

12) Synthesis of Compound (12):

0.3 g (yield: 59%) of the intended compound (12) as a powdery substance was obtained from 0.4 g of the compound (11) and 0.2 g of propionyl chloride in the same manner as that of Synthesis Example 2).

This was a mixture of products having different positions of the acylation, and the products could not be easily separated from each other.

13) Synthesis of Compound (13):

1.8 g of 5,6-dimethyl-2-mercaptobenzimidazole and 2.1 g of diethylene glycol di-p-tosylate were suspended in 20 ml of acetonitrile, and the resultant mixture was heated under reflux in nitrogen stream for 28 hours. After cooling, water was added to the reaction mixture to dissolve the precipitate, and then the mixture was neutralized with 2 N-NaOH. The crystals thus obtained were collected by filtration and washed with acetonitrile to obtain 1.1 g of the intended compound (13) (yield: 52%).

Melting point: 122 to 125° C.; Elementary analysis for $C_{22}H_{26}N_4O_1S_2$: Calculated: C 61.94; H 6.14; N 13.14 (%); Found: C 61.77; H 6.02; N 13.32 (%)

14) Synthesis of Compound (14):

0.74 g of 5-chloro-2-mercaptobenzimidazole and 0.84 g of diethylene glycol di-p-tosylate were suspended in 10 ml of acetonitrile, and the resultant mixture was heated under reflux in nitrogen stream for 28 hours. After cooling, water was added to the reaction mixture to dissolve the precipitate, and then the mixture was neutralized with 2 N-NaOH. The crystals thus obtained were collected by filtration and recrystallized from methanol/acetonitrile (1:5) to obtain 0.4 g of the intended compound (14) (yield: 45%).

Melting point: 90 to 92° C.; Elementary analysis for $C_{18}H_{16}C_{12}N_4O_1S_2$: Calculated: C 49.20; H 3.67; N 12.75 (%); Found: C 49.12; H 3.58; N 12.62 (%)

15) Synthesis of Compound (15):

0.12 g (yield: 55%) of the intended compound (15) as a powdery substance was obtained from 0.16 g of the compound (14) and 0.08 g of propionyl chloride in the same manner as that of Synthesis Example 2).

This was a mixture of products having different positions of the acylation, and the products could not be easily separated from each other.

16) Synthesis of Compound (16):

0.66 g of 5,6-dichloro-2-mercaptobenzimidazole and 0.65 g of diethylene glycol di-p-tosylate were suspended in 8 ml of acetonitrile, and the resultant mixture was heated under reflux in nitrogen stream for 28 hours. After cooling, water was added to the reaction mixture to dissolve the precipitate, and then the mixture was neutralized with 2 N-NaOH. The crystals thus obtained were collected by filtration and recrystallized from methanol/acetonitrile (1:5) to obtain 0.64 g of the intended compound (14) (yield: 84%).

Melting point: 208 to 211° C.; Elementary analysis for $C_{18}H_{14}N_4O_1S_2$: Calculated: C 42.53; H 2.78; N 11.03 (%); Found: C 42.36; H 2.61; N 11.24 (%)

17) Synthesis of Compound (17):

0.15 g (yield: 67%) of the intended compound (15) was obtained from 0.20 g of the compound (16) and 0.08 g of propionyl chloride in the same manner as that of Synthesis Example 2).

Melting point: 134 to 136° C.; Elementary analysis for $C_{24}H_{22}C_{14}N_4O_3S_2$: Calculated: C 46.46; H 3.57; N 9.03 (%); Found: C 46.31; H 3.62; N 9.17 (%)

18) Synthesis of Compound (18)

0.82 g of 5-nitro-2-mercaptobenzimidazole and 1.1 g of diethylene glycol di-p-tosylate were suspended in 15 ml of acetonitrile, and the resultant mixture was heated under reflux in nitrogen stream for 22 hours. After cooling, water was added to the reaction mixture to dissolve the precipitate, and then the mixture was neutralized with 2 N-NaOH. The crystals thus obtained were collected by filtration and washed with acetonitrile to obtain 0.44 g of the intended compound (14) (yield: 58%).

Melting point: 129 to 133° C.; Elementary analysis for $C_{18}H_{16}N_6O_5S_2$: Calculated: C 46.95; H 3.50; N 18.25 (%); Found: C 46.79; H 3.41; N 18.44 (%)

19) Synthesis of Compound (19):

2.4 g (yield: 58%) of the intended compound (19) was obtained from 3.0 g of 2-mercaptobenzimidazole and 4.4 g of triethylene glycol di-p-tosylate in the same manner as that of Synthesis Example 1).

Melting point: 162 to 164° C.; Elementary analysis for $C_{20}H_{22}N_4)_2S_2$: Calculated: C 57.94; H 5.35; N 13.52 (%); Found: C 57.89; H 5.43; N 13.39 (%)

20) Synthesis of Compound (20):

0.34 g (yield: 65%) of the intended compound (20) was obtained from 0.41 g of the compound (19) and 0.2 g of propionyl chloride in the same manner as that of Synthesis Example 2).

Melting point: 135 to 136° C.; Elementary analysis for $C_{26}H_{30}N_4O_4S_2$: Calculated: C 59.29; H 5.74; N 10.64 (%); Found: C 59.18; H 5.55; N 10.71 (%)

21) Synthesis of Compound (21):

0.4 g (yield: 80%) of the intended compound (21) as an oily substance was obtained from 0.4 g of the compound (18) and 0.4 g of propyl bromide in the same manner as that of Synthesis Example 8).

22) Synthesis of Compound (22):

1.5 g of 2-mercaptobenzimidazole and 2.5 g of tetraethylene glycol di-p-tosylate were suspended in 10 ml of acetonitrile. The obtained suspension was heated under reflux in nitrogen stream for 26 hours. After cooling, water was added to the reaction mixture to dissolve the precipitate. After the neutralization with 2 N-NaOH, the oily product thus obtained was extracted with ethyl acetate. The organic later was washed with water, and the solvent was distilled off under reduced pressure. The residue was purified by silica gel column chromatography (silica gel 80 g, solvent: 10% ethyl acetate/chloroform) to obtain 1.8 g (yield: 79%) of the intended compound (22).

EXAMPLE 3

The effects of antihyperlipemic agents and antiarteriosclerotic agents each containing a benzimidazole derivative represented by the formula III of the present invention were examined as will be described below.

Pharmacological Tests (1) In vitro tests on inhibition of foaming of macrophage with mouse peritoneal macrophage:

The necks of 15-week old female ICR mice (Japan SLC) were cut off. After blood-letting, Hanks buffer solution (Nissui Seiyaku Co., Ltd.) was injected into the abdominal cavity of each mouse. The abdomen was massaged and then the buffer solution was rapidly recovered, centrifuged at 1000 rotations for 5 minutes to collect the peritoneal macrophages. The peritoneal macrophases thus collected were then suspended in GIT medium (Wako Pure Chemical Industries, Ltd.), and the suspension was spread on a 24-hole microplate. After the cultivation at 37° C. in 5% $CO_2$ for 2 hours, the medium was replaced with a Dulbecoo Modified Eagle's MEM medium (Nissui Seiyaku Co., Ltd.). After the cultivation at 37° C. in 5% $CO_2$ for additional 16 hours, the following substances were added in the following order:

(1) subject: dissolved in DMSO (Wako Pure Chemical Industries, Ltd.)
(2) Liposome:
PC/PS/DCP/CHOL.=50/50/10/75 (nmols)
PC: phosphatidyl choline (a product of Funakoshi)
PS: phosphatidyl serine (ditto)
DCP: dicetyl phosphate (ditto)
CHOL.: cholesterol (Sigma).

After further cultivation at 37° C. in 5% $CO_2$ for 16 hours, the lipid fraction was extracted with chloroform and methanol. The lipid fraction thus extracted was dissolved in isopropyl alcohol, and the formed cholesteryl ester (CE) was determined by an enzymatic coloring method. The cholesteryl ester-forming rate of each compound was calculated in terms of the ratio thereof to the control. The cytotoxicity was examined by microscopic observation of the shape of the cell.

The results are given in Table 2.

TABLE 1

| Compound No | Dose ($\mu$M) | CE (%) | Cytotoxicity |
|---|---|---|---|
| (1) | 5 | 25 | none |
| (2) | 5 | 7 | none |
| (3) | 5 | 15 | none |
| (4) | 5 | 19 | none |
| (5) | 5 | 20 | none |
| (6) | 5 | 26 | none |
| (7) | 5 | 74 | none |
| (8) | 5 | 16 | none |
| (9) | 5 | 28 | none |
| (10) | 5 | 76 | none |
| (11) | 5 | 38 | none |
| (12) | 5 | 19 | none |
| (13) | 5 | 45 | none |
| (14) | 5 | 18 | none |
| (15) | 5 | 17 | none |
| (16) | 5 | 46 | none |
| (17) | 5 | 27 | none |

TABLE 1-continued

| Compound No | Dose ($\mu$M) | CE (%) | Cytotoxicity |
|---|---|---|---|
| (18) | 5 | 10 | none |
| (19) | 5 | 11 | none |
| (20) | 5 | 69 | none |
| (21) | 5 | 23 | none |
| (22) | 5 | 22 | none |

It is apparent from Table 1 that when the compounds were administered in a dose of 5 $\mu$m, no cytotoxicity was exhibited. Namely, it is apparent that these compounds have only a low toxicity and are capable of remarkably reducing the CE-formation rate. Namely, these compounds remarkably inhibit the foaming of macrophases without exhibiting a high toxicity to the macrophages.

(2) Effect of reducing blood lipid of rabit having high-cholesterol feed:

A high-cholesterol food (100 g/day/rabbit: ORC-4 of Oriental Yeast Co., Ltd. +0.5% cholesterol +0.5% olive oil) was given to each of male New Zealand white rabbits weighing about 2 kg for seven days to make them suffer from hypercholesterolemia.

In the next stage, the high-cholesterol food was still given to the rabbits and, in addition, 30 mg/kg/day/rabbit of the test compound (2) was continuously given in the form of a mixture thereof with the food to a group of three rabbits (test group) for 14 days. On the other hand, only the same high-cholesterol food as above was given in the equal dose to another group of three rabbits (control group).

After the continuous feeding for 14 days followed by fasting for one day, a small amount of the blood was taken from the parotid vein to determine the total blood cholesterol (latripo TC: a product of latron Co. Ltd.).

As for the total blood cholesterol decreasing rate, it was 25% based on the control (three rabits) to which no medicine was given.

Thus, it was apparent that the test compound (2) has an excellent blood cholesterol decreasing effect.

(3) Acute Toxicity Test:

The compound (2) was suspended in 0.5% Tween 80 solution. The suspension was orally administered to a group of six 8-week ddy mice, and the acute toxcity was observed for one month to find that $LD_{50}$ of the compound (2) was 5,000 mg/kg or above. This fact indicates that the compound of the present invention has only a low toxicity.

Example 4

The pharmacological effects of the compounds given in Table 2 were evaluated in the same manner as that of Example 3.

TABLE 2

| Compound No | Dose ($\mu$M) | CE (%) | Cytotoxicity |
|---|---|---|---|
| I-7 | 5 | 28 | none |
| IV-1 | 5 | 28 | none |
| IV-2 | 5 | 28 | none |
| IV-3 | 5 | 38 | none |
| I-1 | 5 | 45 | none |
| IV-4 | 5 | 79 | none |
| I-3 | 5 | 21 | none |
| IV-5 | 5 | 11 | none |
| IV-8 | 5 | 46 | none |
| I-2 | 5 | 62 | none |
| I-4 | 5 | 35 | none |

TABLE 2-continued

| Compound No | Dose (μM) | CE (%) | Cytotoxicity |
|---|---|---|---|
| IV-13 | 5 | 22 | none |
| IV-14 | 5 | 32 | none |
| II-1 | 5 | 41 | none |
| II-2 | 5 | 46 | none |
| II-4 | 5 | 75 | none |
| II-5 | 5 | 81 | none |
| II-6 | 5 | 80 | none |
| II-8 | 5 | 78 | none |
| II-9 | 5 | 52 | none |
| II-10 | 5 | 45 | none |
| II-11 | 5 | 34 | none |
| II-12 | 5 | 45 | none |
| II-13 | 5 | 38 | none |
| II-14 | 5 | 18 | none |
| II-15 | 5 | 38 | none |
| II-20 | 5 | 52 | none |
| II-28 | 5 | 46 | none |
| II-29 | 5 | 28 | none |
| II-30 | 5 | 42 | none |
| II-31 | 5 | 80 | none |
| II-32 | 5 | 78 | none |
| II-33 | 5 | 25 | none |
| II-34 | 5 | 35 | none |
| II-35 | 5 | 31 | none |
| II-36 | 5 | 21 | none |

It is apparent from the results given in Table 2 that 5 μm of each of these compounds was not cytotoxic. In other words, it is apparent that these compounds have only a low toxicity and is capable of remarkably inhibiting the CE formation rate. Namely, they remarkably inhibit the foaming of macrophages without exhibiting a high toxicity to the macrophases.

(ii) Acute Toxicity Test:

The compound I-7 was suspended in 0.5% Tween 80 solution. The suspension was orally administered to a group of six 8-week ddy mice, and the acute toxcity was observed for one month to find that $LD_{50}$ of this compound was 5,000 mg./kg or above. This fact indicates that the compound of the present invention has only a low toxicity.

EXAMPLE 5 TABLETS

Preparation of tablets each containing 25 mg of compound (1) or I-7:

| | | |
|---|---|---|
| (1) Compound (1) or I-7 | 10 g | |
| (2) Corn starch | 40 g | |
| (3) Crystalline cellulose | 45 g | |
| (4) Carboxymethylcellulose calcium | 4 g | |
| (5) Light anhydrous silicic acid | 500 mg | |
| (6) Magnesium stearate | 500 mg | |
| Total | 100 g | |

The above-described components (1) to (6) were homogeneously mixed together. The mixture was compression-molded with a tableting machine to obtain tablets each weighing 250 mg. The tablet contained 25 mg of the compound (1) or I-7. The dosage for adults is: 5 to 30 tablets/day to be taken several times a day.

EXAMPLE 6 CAPSULES

Preparation of capsules each containing 40 mg of compound (1) or I-7:

| | | |
|---|---|---|
| (1) Compound (1) or I-7 | 20 g | |
| (2) Corn starch | 79.5 g | |
| (3) Anhydrous sinnamic acid | 500 mg | |
| Total | 100 g | |

The above-described components (1) to (3) were homogeneously mixed together. A capsule was filled with 200 mg of the mixture. Each capsule contained 40 mg of the compound (1) or I-7. The dosage for adults is: 1 to 20 tablets/day to be taken several times a day.

EXAMPLE 7 GRANULES

Preparation of granules containing 100 mg/g of compound (1) or I-7:

| | | |
|---|---|---|
| (1) Compound (1) or I-7 | 10 g | |
| (2) Crystalline cellulose | 40 g | |
| (3) 10% solution of hydroxypropyl-cellulose in ethanol | 50 g | |
| Total | 100 g | |

The above-described components (1) to (3) were homogeneously mixed and kneaded together. The mixture was granulated with an extrusion granulating machine and then dried to obtain granules. The granules contained 100 mg/g of the compound (1) or I-7. The dosage for adults is: 1 to 8 g/day to be taken several times a day.

What is claimed is:

1. A method for inhibiting hyperlipemia or atherosclerosis comprising administering an effective amount of a 2-mercaptobenzimidazole compound represented by formula IV:

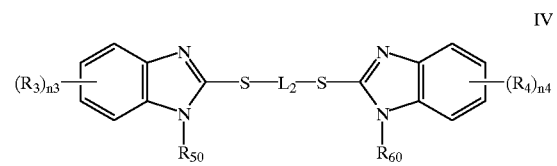

wherein $R_3$ and $R_4$ each represent a hydrogen atom, a halogen atom, or an alkyl, alkoxy, alkoxycarbonyl, carbamoyl, sulfamoyl, acylamino, sulfonylamino, cyano or nitro group;

$R_{50}$ and $R_{60}$ each represent a hydrogen atom, alkyl group, or acyl group;

$n_3$, $n_4$, each represent 1 or 2; and $L_2$ represents a connecting group which is an alkylene group or a phenylene group-containing an alkylene group, or a pharmaceutically acceptable salt thereof, to a mammal.

2. The method of claim 1, wherein the 2-mercaptobenzimidazole compound is a compound represented by formula IV-a:

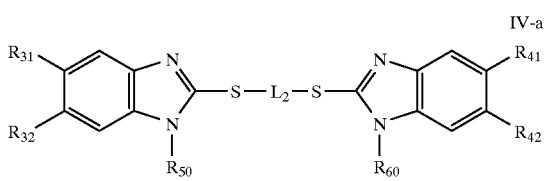

IV-a wherein $L_2$, $R_{50}$ and $R_{60}$ are as defined in claim 1, $R_{31}$ and $R_{32}$ are the same as $R_3$, and $R_{41}$ and $R_{42}$ are the same as $R_4$.

3. The method of claim 2, wherein $R_{31}$, $R_{32}$, $R_{41}$, $R_{42}$, $R_{50}$ and $R_{60}$ in formula IV-a are hydrogen, and $L_2$ is an alkylene group having 4 to 10 carbon atoms or an alkylene-phenylene-alkylene group wherein each alkylene moiety of the alkylene-phenylene-alkylene group has 1 to 2 carbon atoms.

4. The method of claim 2, wherein one of $R_{31}$ and $R_{32}$ and one of $R_{41}$ and $R_{42}$ in formula IV-a are hydrogen, and the other one of $R_{31}$ and $R_{32}$ and the other one of $R_{41}$ and $R_{42}$ are lower alkyl, halogen, nitro or lower acylamino, and $R_{50}$ and $R_{60}$ are hydrogen, lower alkyl or lower alkanoyl.

5. The method of claim 2, wherein $R_{31}$, $R_{32}$, $R_{41}$ and $R_{42}$ in formula IV-a are halogen, and $R_{50}$ and $R_{60}$ are hydrogen.

6. The method of claim 2, wherein $R_{31}$, $R_{32}$, $R_{41}$ and $R_{42}$ in formula IV-a are hydrogen, and $R_{50}$ and $R_{60}$ are lower alkanoyl or lower alkyl, and $L_2$ is an alkylene group having 4 to 10 carbon atoms or an alkylene-phenylene-alkylene group, wherein each alkylene moiety of the alkylene-phenylene-alkylene group has 1 to 2 carbon atoms.

7. The method of claim 2, wherein $R_{31}$, $R_{32}$, $R_{41}$ and $R_{42}$ in formula IV-a are halogen or lower alkyl, and $R_{50}$ and $R_{60}$ are lower alkanoyl or lower alkyl.

8. A method for therapy of hyperlipemia or atherosclerosis in a mammal comprising administering an effective amount of a 2-mercaptobenzimidazole compound represented by formula IV:

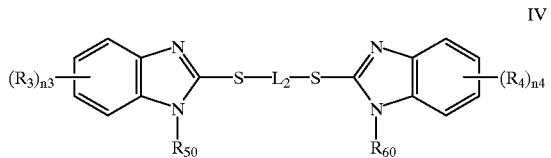

IV wherein $R_3$ and $R_4$ each represent a hydrogen atom, halogen atom, or alkyl, alkoxy, alkoxycarbonyl, carbamoyl, sulfamoyl, acylamino, sulfonylamino, cyano or nitro group;

$R_{50}$ and $R_{60}$ each represent a hydrogen atom, alkyl group, or acyl group;

$n_3$, $n_4$ each represent 1 or 2; and, $L_2$ represents a connecting group which is an alkylene group or phenylene group-containing alkylene group, or a pharmaceutically acceptable salt thereof, to a mammal.

9. A method for inhibiting foamy macrophages in a mammal comprising contacting a foamy macrophage with an effective amount of a 2-mercaptobenzimidazole compound represented by formula IV:

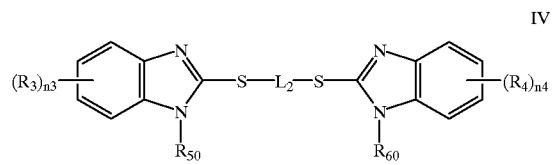

IV wherein $R_3$ and $R_4$ each represent a hydrogen atom, a halogen atom, or an alkyl, alkoxy, alkoxycarbonyl, carbamoyl, sulfamoyl, acylamino, sulfonylamino, cyano or nitro group;

$R_{50}$ and $R_{60}$ each represent a hydrogen atom, alkyl group, or acyl group;

$n_3$, $n_4$ each represent 1 or 2; and $L_2$ represents a connecting group which is an alkylene group or a phenylene group-containing an alkylene group, or a pharmaceutically acceptable salt.

10. A method for reducing the formation of cholesteryl ester in foamy macrophages in a mammal comprising contacting a foamy macrophage with an effective amount of a 2-mercaptobenzimidazole compound represented by formula IV:

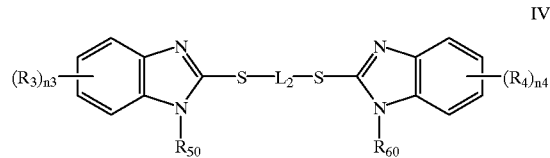

IV wherein $R_3$ and $R_4$ each represent a hydrogen atom, a halogen atom, or an alkyl, alkoxy, alkoxycarbonyl, carbamoyl, sulfamoyl, acylamino, sulfonylamino, cyano or nitro group;

$R_{50}$ and $R_{60}$ each represent a hydrogen atom, alkyl group, or acyl group;

$n_3$, $n_4$ each represent 1 or 2; and $L_2$ represents a connecting group which is an alkylene group or a phenylene group-containing an alkylene group, or a pharmaceutically acceptable salt thereof.

* * * * *

UNITED STATES PATENT AND TRADEMARK OFFICE
CERTIFICATE OF CORRECTION

PATENT NO. : 5,962,493
DATED : October 5, 1999
INVENTOR(S) : Aoki et al.

It is certified that error appears in the above-identified patent and that said Letters Patent is hereby corrected as shown below:

On the Title page, after box [62], delete text beginning "Division of" through text ending "abandoned" and insert the following:
 --Divisional application of U.S. Serial No. 08/669,516, filed on July 12, 1996, now abandoned, which was a 35 U.S.C. §371 filing of PCT/JP95/00116, filed on January 30, 1995--

Under "References Cited - U.S. PATENT DOCUMENTS" on the cover page, the following reference should be inserted after the line referring to "3,704,130":
 --5,290,801  3/1994  Higley et al.  514/395--

Under "FOREIGN PATENT DOCUMENTS" on the cover page, the following references should be inserted before the line referring to "0520552 A1":
 --DE 3023432  1/1981  Germany
 DE 3608032  9/1986  Germany--

Signed and Sealed this

Sixteenth Day of January, 2001

Attest:

Q. TODD DICKINSON

*Attesting Officer*   *Commissioner of Patents and Trademarks*